US009501888B1

(12) United States Patent
Morad et al.

(10) Patent No.: US 9,501,888 B1
(45) Date of Patent: Nov. 22, 2016

(54) VENDING MACHINE FOR RETAINING AND DISPENSING FEMININE HYGIENE PRODUCTS THROUGH A NOVEL COIN OPERATING APPARATUS

(71) Applicants: Fred I. Morad, Toluca, CA (US); William P. Camp, Jr., Wooster, OH (US); Arnold G. Benecke, Crawfordsville, IN (US); Robert A. Acosta, Norwalk, CA (US)

(72) Inventors: Fred I. Morad, Toluca, CA (US); William P. Camp, Jr., Wooster, OH (US); Arnold G. Benecke, Crawfordsville, IN (US); Robert A. Acosta, Norwalk, CA (US)

(73) Assignee: Worldwide Integrated Resources, Inc., Montebello, CA (US)

( * ) Notice: Subject to any disclaimer, the term of this patent is extended or adjusted under 35 U.S.C. 154(b) by 0 days.

(21) Appl. No.: 15/143,619

(22) Filed: May 1, 2016

(51) Int. Cl.
| | | |
|---|---|---|
| *G08B 21/18* | (2006.01) |
| *G07F 11/04* | (2006.01) |
| *G07F 9/04* | (2006.01) |
| *G07F 5/02* | (2006.01) |
| *G07F 11/10* | (2006.01) |
| *G07F 11/22* | (2006.01) |
| *A61F 13/551* | (2006.01) |

(52) U.S. Cl.
CPC ....... *G07F 11/045* (2013.01); *A61F 13/55135* (2013.01); *A61F 13/55175* (2013.01); *G07F 5/02* (2013.01); *G07F 9/04* (2013.01); *G07F 11/10* (2013.01); *G07F 11/22* (2013.01); *G08B 21/182* (2013.01)

(58) Field of Classification Search
CPC .......................................................... A47F 1/00
See application file for complete search history.

(56) References Cited

U.S. PATENT DOCUMENTS 7,469,779 B2  12/2008 Horian
7,950,513 B2   5/2011 Horian

*Primary Examiner* — Ayodeji Ojofeitimi
(74) *Attorney, Agent, or Firm* — Thomas I. Rozsa

(57) ABSTRACT

A vending machine that dispense feminine hygiene products. Specifically, this invention is a coin-operated vending machine that dispenses sanitary napkins and tampons. This invention allows a user to purchase a feminine hygiene product by placing a coin or multiple coins in a slot within the vending machine and pressing a product release button. The product is then dispensed to the consumer. The apparatus also provides a mechanism for retrieving a coin in the event that the vending machine is out of a specific feminine hygiene product sought to be purchased. The invention also provides for the ability to have a vending machine that does not require any coin to be inserted in order to obtain the feminine hygiene product.

1 Claim, 24 Drawing Sheets

VENDING MACHINE FOR RETAINING AND DISPENSING FEMININE HYGIENE PRODUCTS THROUGH A NOVEL COIN OPERATING APPARATUS

BACKGROUND OF THE INVENTION

1. Field of the Invention

The present invention relates to vending machines that dispense feminine hygiene products. Specifically, this invention relates to a coin-operated vending machine that dispenses sanitary napkins and tampons.

2. Description of the Prior Art

There are coin drop mechanisms and coin-operated release machines in various forms in the prior art. These previous inventions vary in sophistication and efforts to prevent against theft, weather conditions, and durability. Numerous inventions within the prior art prevent fraud by having complex electronic or mechanical schemes to authenticate currency. Other less complex coin drop mechanisms or coin-operated release machines require the user to rotate a handle by twisting a rotatable lever. This rotation is often impossible for users who are incapable of twisting their wrists and applying torque pressure while twisting. There are very limited prior inventions that have a pushbutton coin-operated release as found in this invention.

The following two (2) patents are relevant to the present invention:

1. U.S. Pat. No. 7,469,779 issued to James G. Horian on Dec. 30, 2008 for "Coin Drop Mechanism".
2. U.S. Pat. No. 7,950,513 issued to James G. Horian on May 31, 2011 for "Coin Drop Mechanism".

Therefore, there is a significant need for an improved invention which is mechanically simple, but functionally complete to allow a user or consumer to dispense a product using a coin-operated machine without requiring the user to twist or apply torque pressure to the coin-operated machine

SUMMARY OF THE INVENTION

The present invention is a coin-operated machine that dispenses feminine hygiene products. This coin-operated vending machine functions by having a slot opening where a coin is inserted. When the coin is inserted, a pushbutton is then pushed to force a product out of a storage holder and onto a release tray. All the components of the coin-operated vending machine are mechanical except for an electronic sensor that notifies the end user through illumination of a red light that the vending machine is out of product. The present invention relates to vending machines that dispense feminine hygiene products. Specifically, this invention relates to a coin-operated vending machine that dispenses sanitary napkins and tampons. This invention allows a user to purchase a feminine hygiene product by placing a coin or multiple coins or no coins in a slot within the vending machine and pressing a product release button. The product is then dispensed to the consumer.

The mechanical functioning components of the vending machine and the products to be dispensed are primarily found within the present inventions cabinet interior. The external components of the vending machine such as the release tray and the moveable pushbuttons are found on the front of the invention.

It is an object of the present invention is to provide an apparatus to hold and dispense two products. These two products are sanitary napkins and tampons. The pushbutton release mechanisms used to release these two products are predominantly the same with small differences that will be explained in the detailed description of the embodiments section.

It is a further object of the present invention to provide a predominantly mechanical device for dispensing feminine hygiene products that does not require the rotation of a handle. This can be difficult or impossible for individuals with physical limitations.

It is an additional object of the present invention to allow the operator or owner of the vending machine to select the number of coins required to dispense a product. The amount of currency required to purchase a product can vary from being free (no coins) to up to fifty cents in quarters. It is also within the spirit and scope of this invention to have a higher range of cost which could be achieved by the use of one dollar coins. Further, this invention can be used with foreign currencies with slight modifications to the coin slot assembly.

It is an additional object of the present invention to provide a simple mechanical device that dispenses feminine hygiene products without the risk of quarters becoming lodged or stuck in the vending machine during operation. Some prior art coin drop mechanisms involve elaborate schemes to channel the quarter from an upper quarter insert location to lower internal components of the vending machine. This creates inherent possibilities for the quarter to be stuck inside of the vending machine. Further, there is an additional cost to having numerous components within a vending machine which are necessary to channel the quarter and these additional components increase the chance of at least one malfunction of an additional component.

It is a further object of the present invention to provide a user friendly, low maintenance, easy-to-operate feminine hygiene product dispenser. As discussed above, the only electrical components of the present invention are sensors to visually notify when the invention is out of one of the products. The present invention is designed to dispense tampons and sanitary napkins to users when a quarter is inserted into the vending machine. The push buttons for each of the products require less than five (5) pounds of force to be pushed in and dispense a product which is a requirement of ADA (American Disability Act). Each of the two products is released when each respective pushbutton is depressed. After the quarter (or quarters depending upon the preference of the owner of the facility where the present invention is located) is selected, the user inserts the quarter into one of the open slots in the lower front portion of the vending machine. The quarter is inserted between two movable support members. These members are a coin return release and a cam. After the coin is inserted and the cam rotates, a portion of a hole partially covered by the cam is opened, exposing more of the hole. This allows the coin slot plate with pushbutton attached to move inwards towards the center of the vending machine. As the coin slot plate moves inward, a protruding member which fits through the exposed hole forces the cam to rotate and expose even more of the hole. As the cam rotates counterclockwise exposing more of the hole, the distance between the cam and the coin return wall becomes greater and the quarter is no longer held in place. This causes the quarter to pass thorough the slot opening and into the coin collector box.

For the tampon product, the push button is pushed inward towards the center of the invention. The push button when pushed displaces the tampon pusher to move inwards and away from the front of the vending machine. The tampon pusher when displaced then comes into direct contact with the tampon and pushes the tampon off of a tampon storage shelf and drops the tampon onto the release tray where the user can retrieve the product.

Similarly, for the sanitary napkin product after the coin(s) is inserted, the push button is pushed inward towards the center of the vending machine. The push button when pushed displaces a push rod. The push rod is connected by interlocking tongue and groove teeth to a pinion gear which rotates the pinion gear as the push rod moves away from the front of the vending machine towards the center of the vending machine. This causes the sanitary napkin tray to rotate, which forces one of the sanitary napkin boxes to drop onto the release tray where the user can reach, remove from the vending machine and then use the product.

It is further object of the present invention to have a product weight for each of the two products. Therefore, included inside of the vending machine is a tampon weight and a sanitary napkin weight. These weights provide three functions. First, a respective weight forces each respective individual product downward onto a respective storage shelf and in position for the dispensing mechanism to engage the product. Second, each of the weights has a magnet attached to the weight which when the weight comes in contact with a sensor completes an electrical circuit which notifies the user by means of an LED light that a product is no longer available. This visibly alerts the user that the vending machine is empty of tampons or sanitary napkins, or both. It also alerts the attendant that the vending machine needs to be filled with the product without requiring the attendant to open the door and visibly check. Lastly, when the product weights are at the bottom of the hopper or reservoir, it blocks the coin-operated pushbutton from moving forward. Therefore, coins will not drop into the coin collection box and can be retrieved through a coin return plate.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

Figures 14, 15:
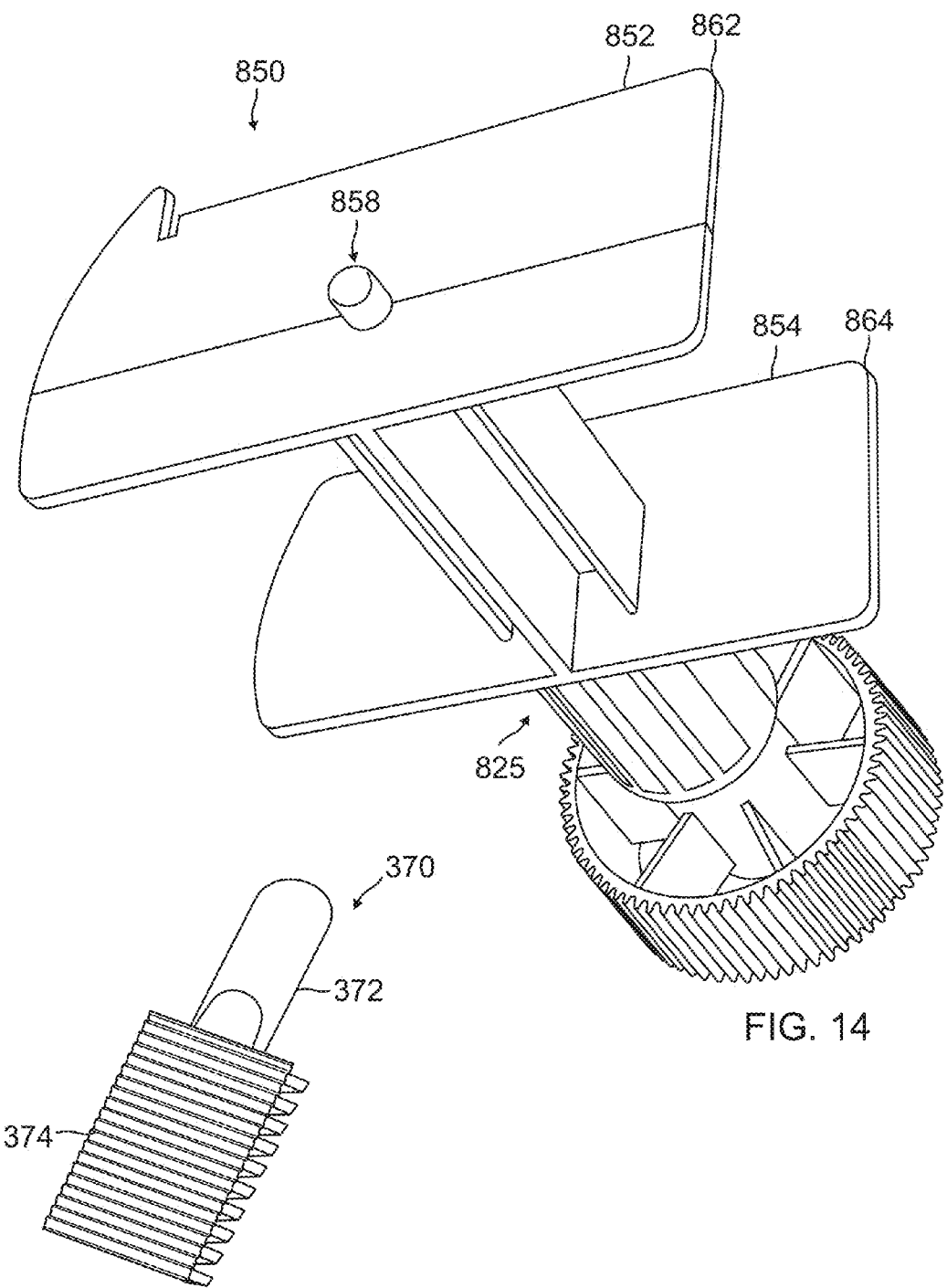
Figure 16:
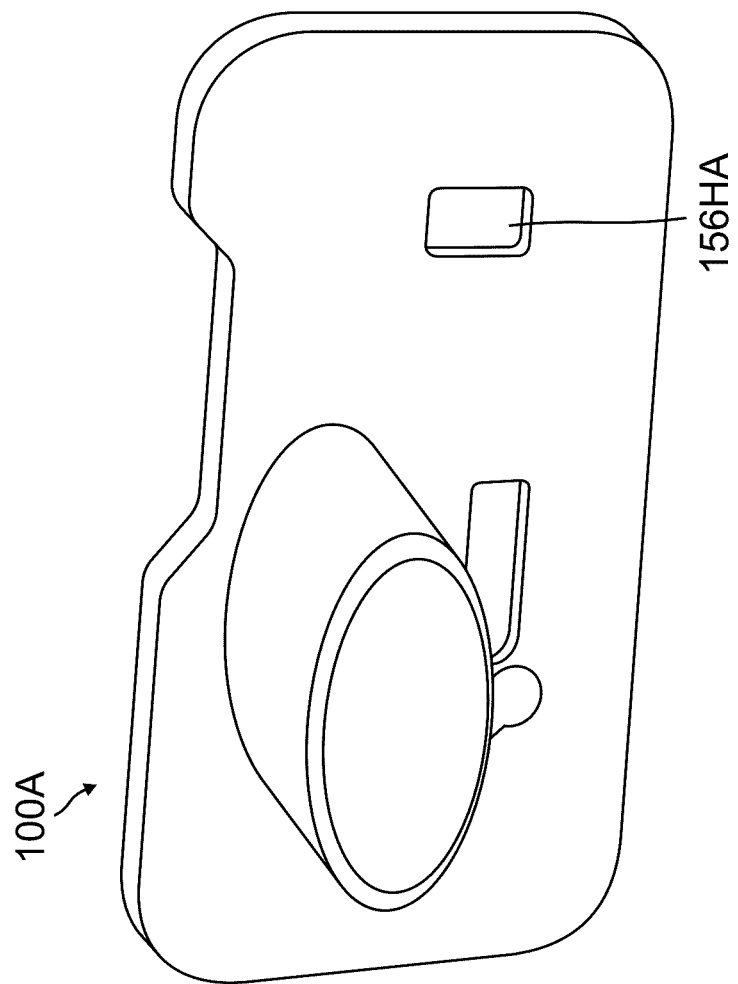
Figure 17:
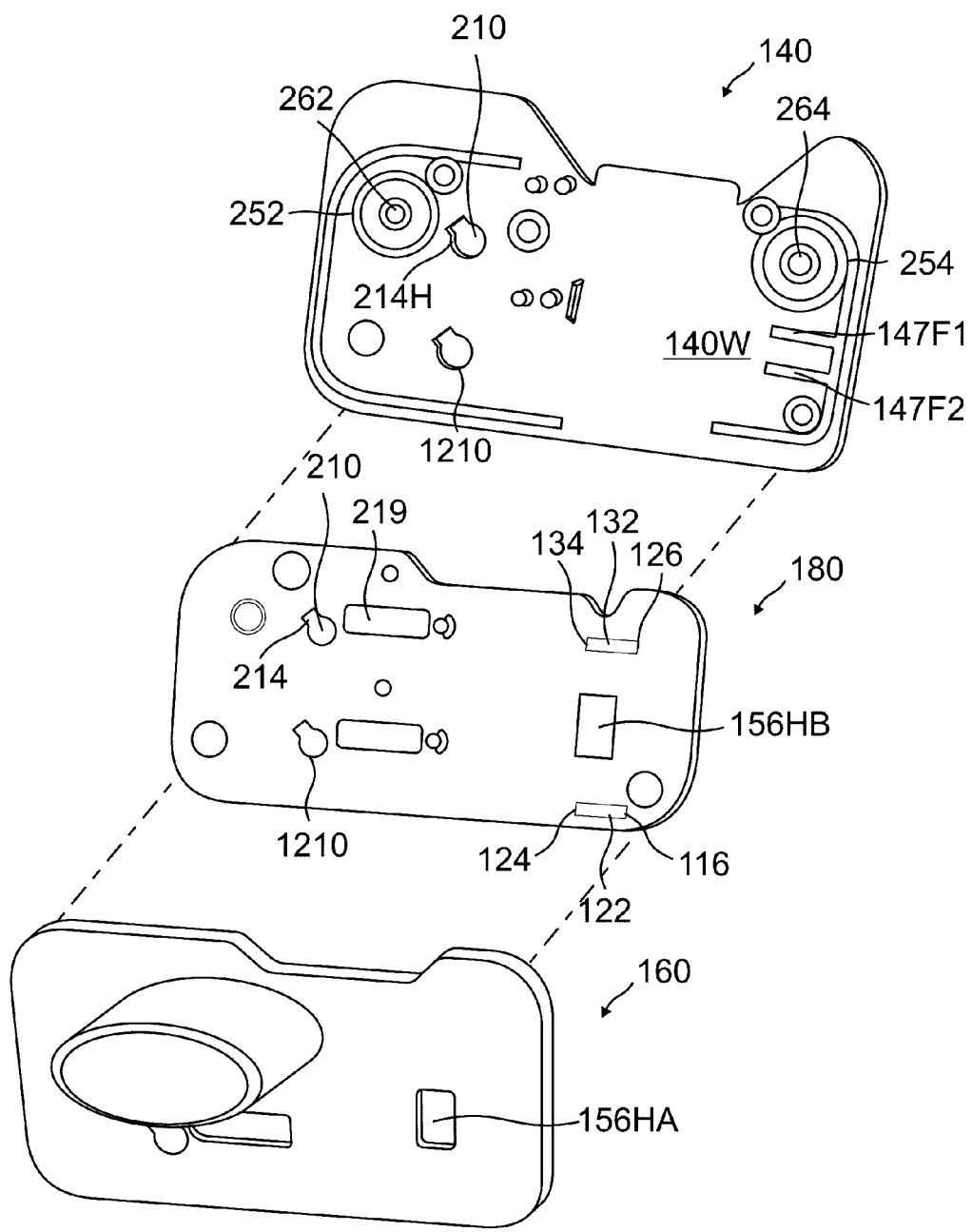
Figure 18:
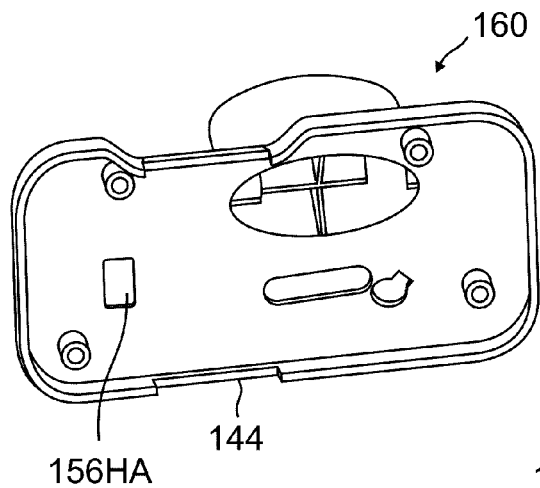
Figure 19:
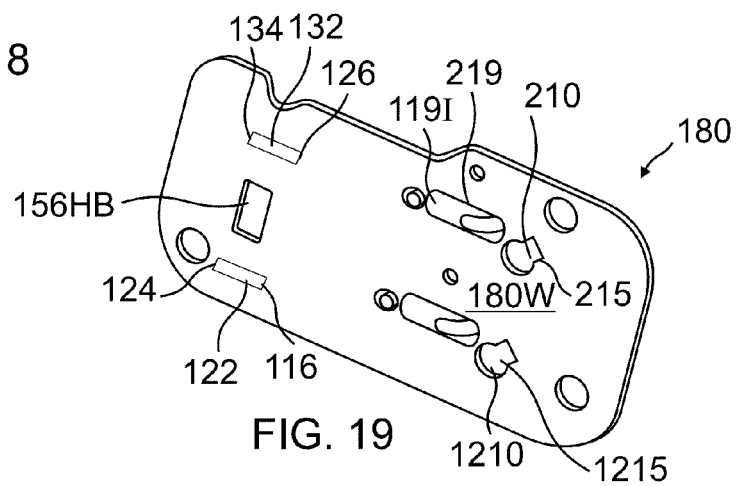
Figure 20:
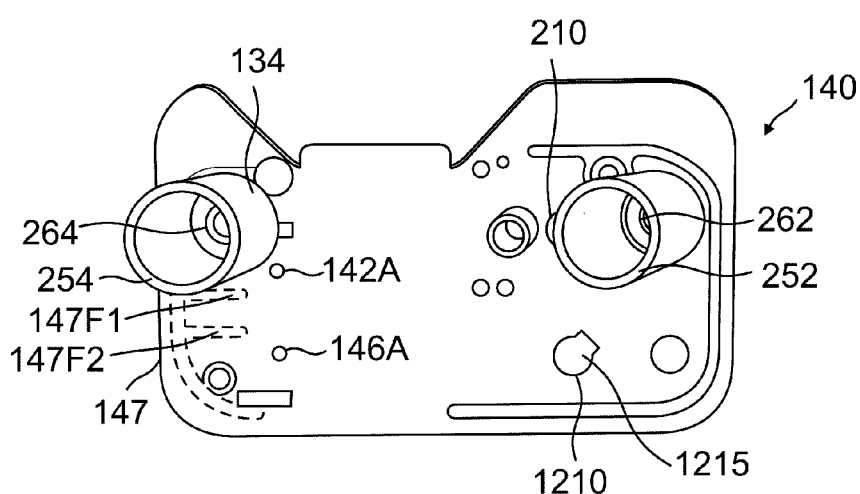
Figure 21:
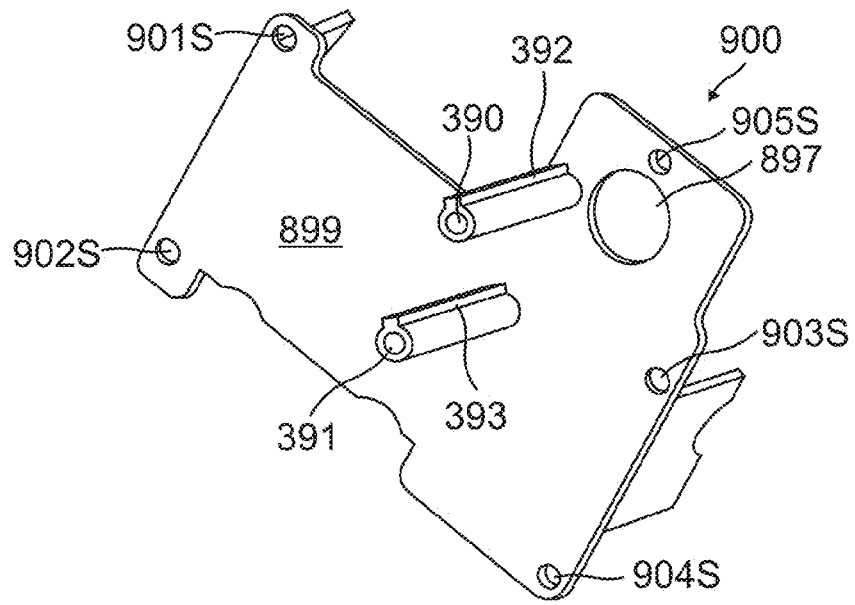
Figure 22:
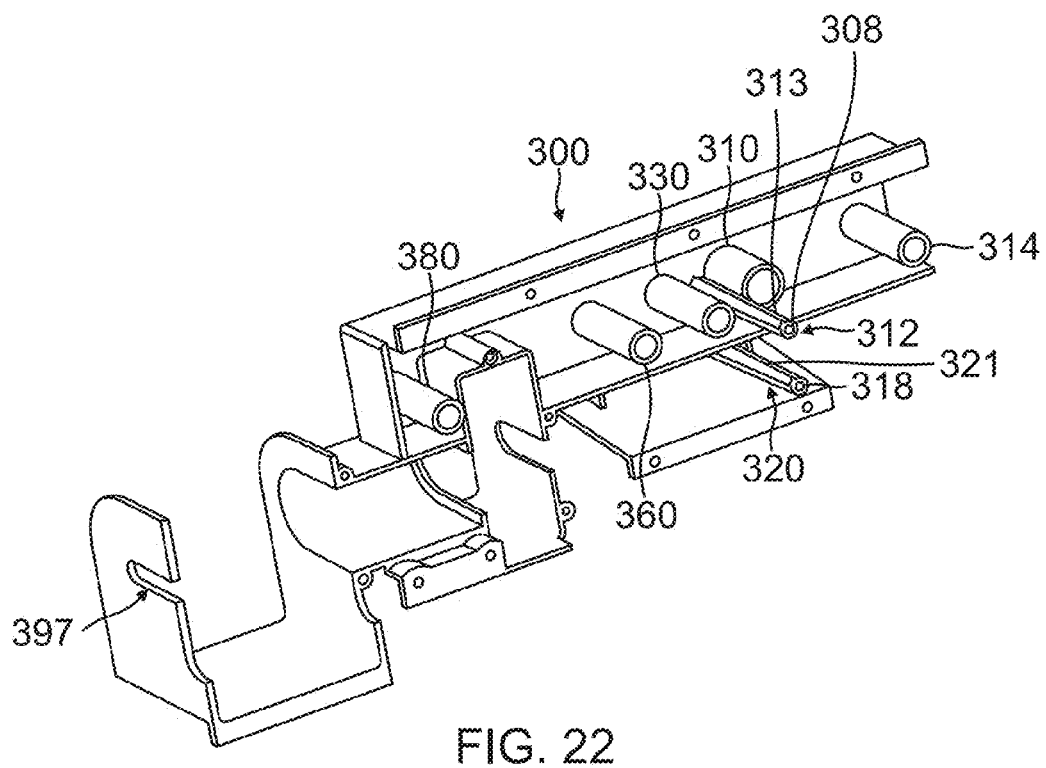
Figure 23:
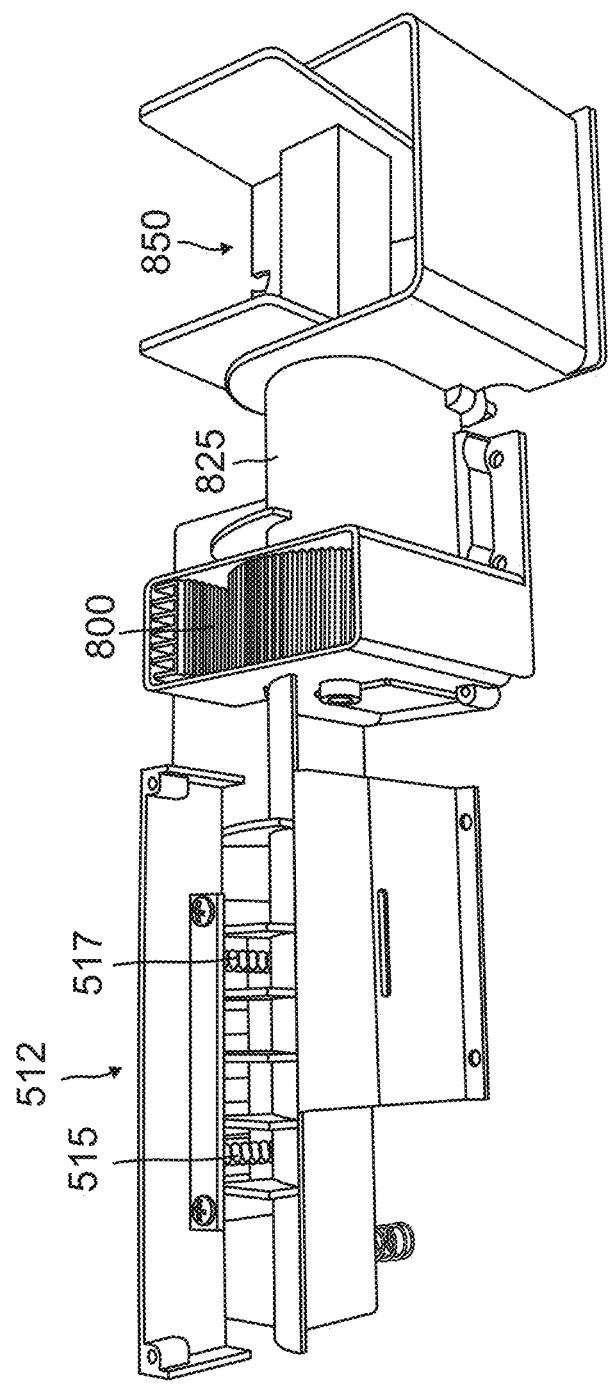
Figure 24:
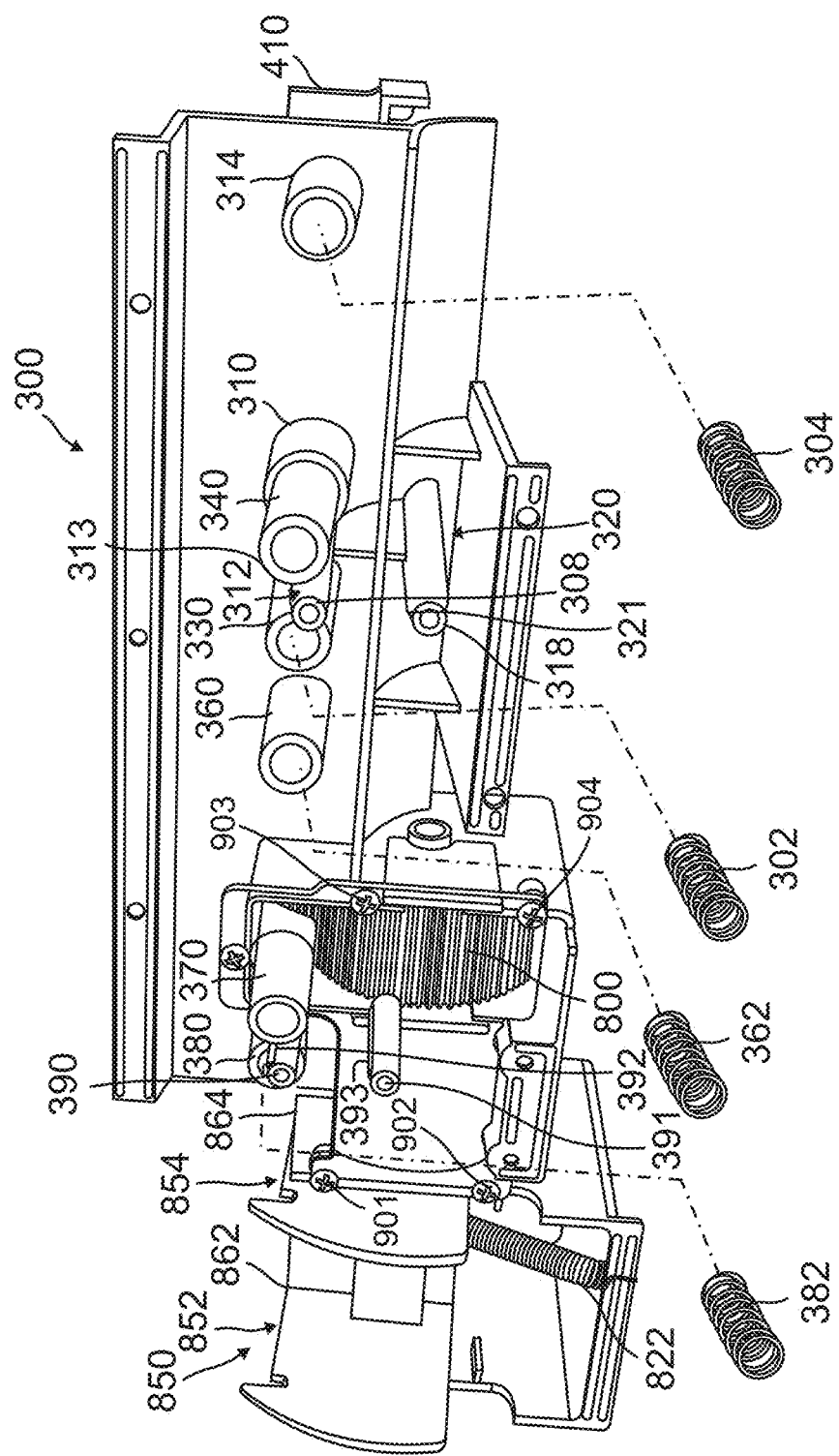
Figure 25:
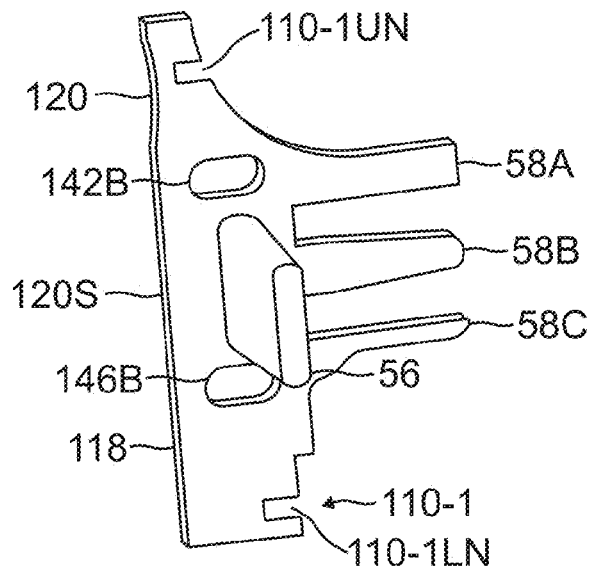
Figure 26:
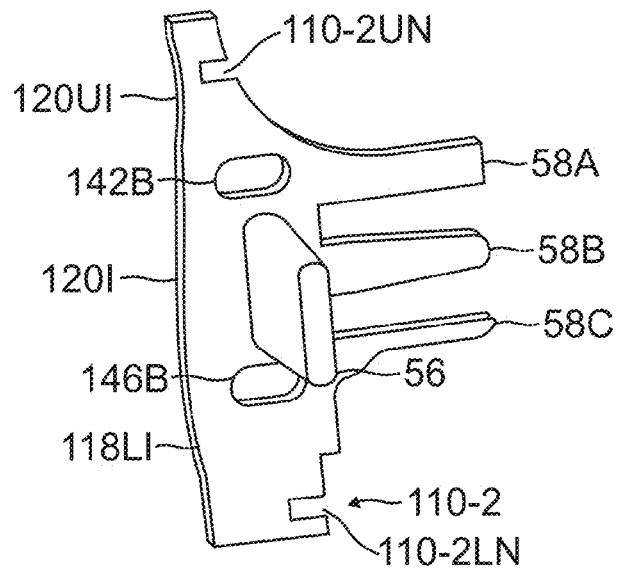
Figure 27:
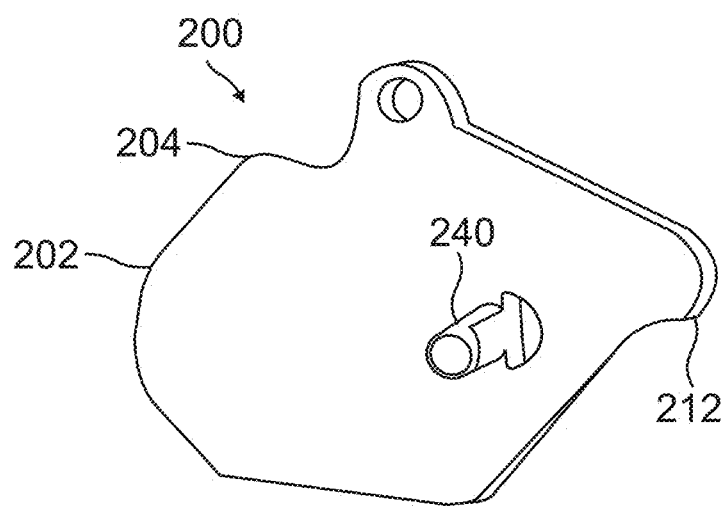
Figure 28:
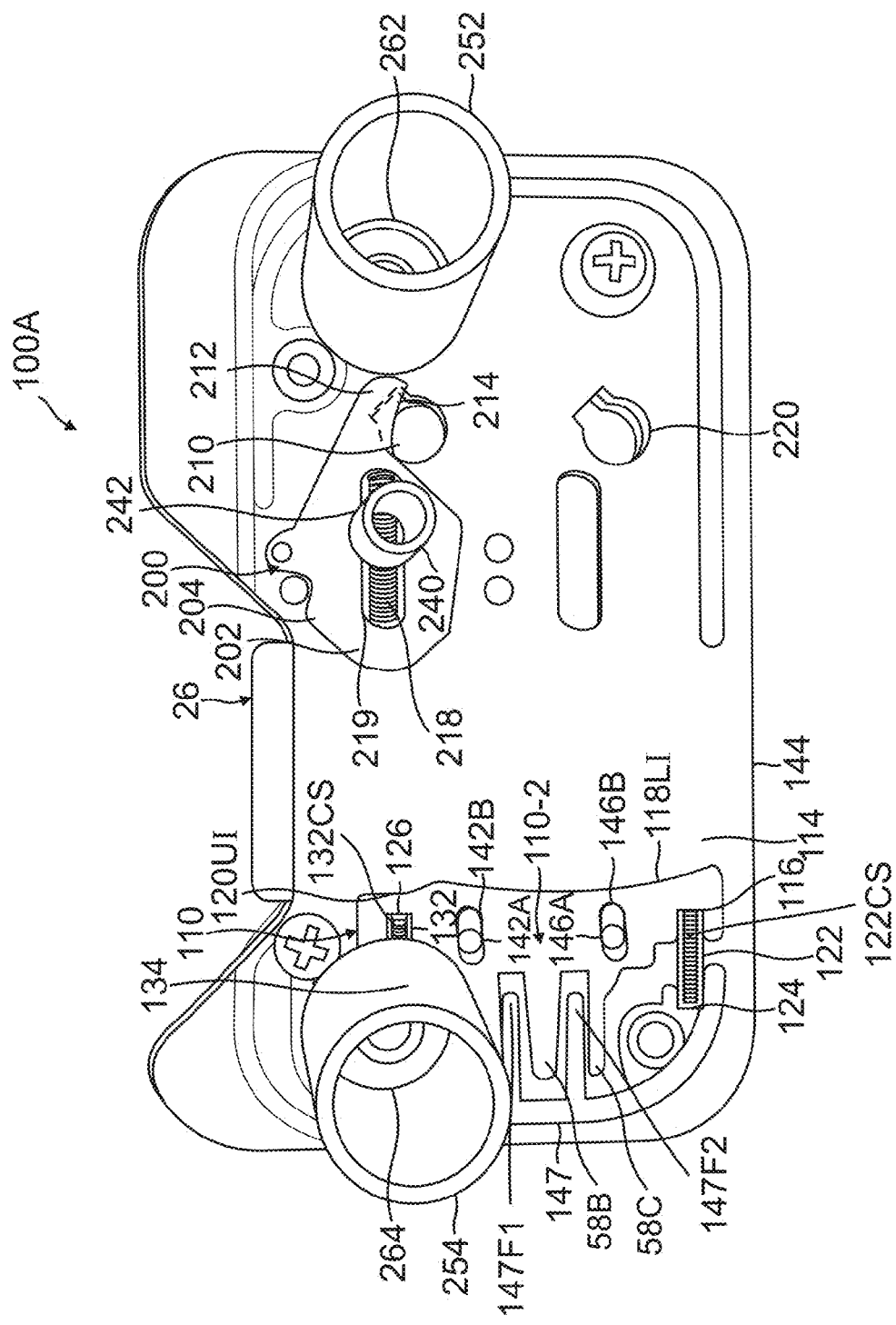
Figure 29:
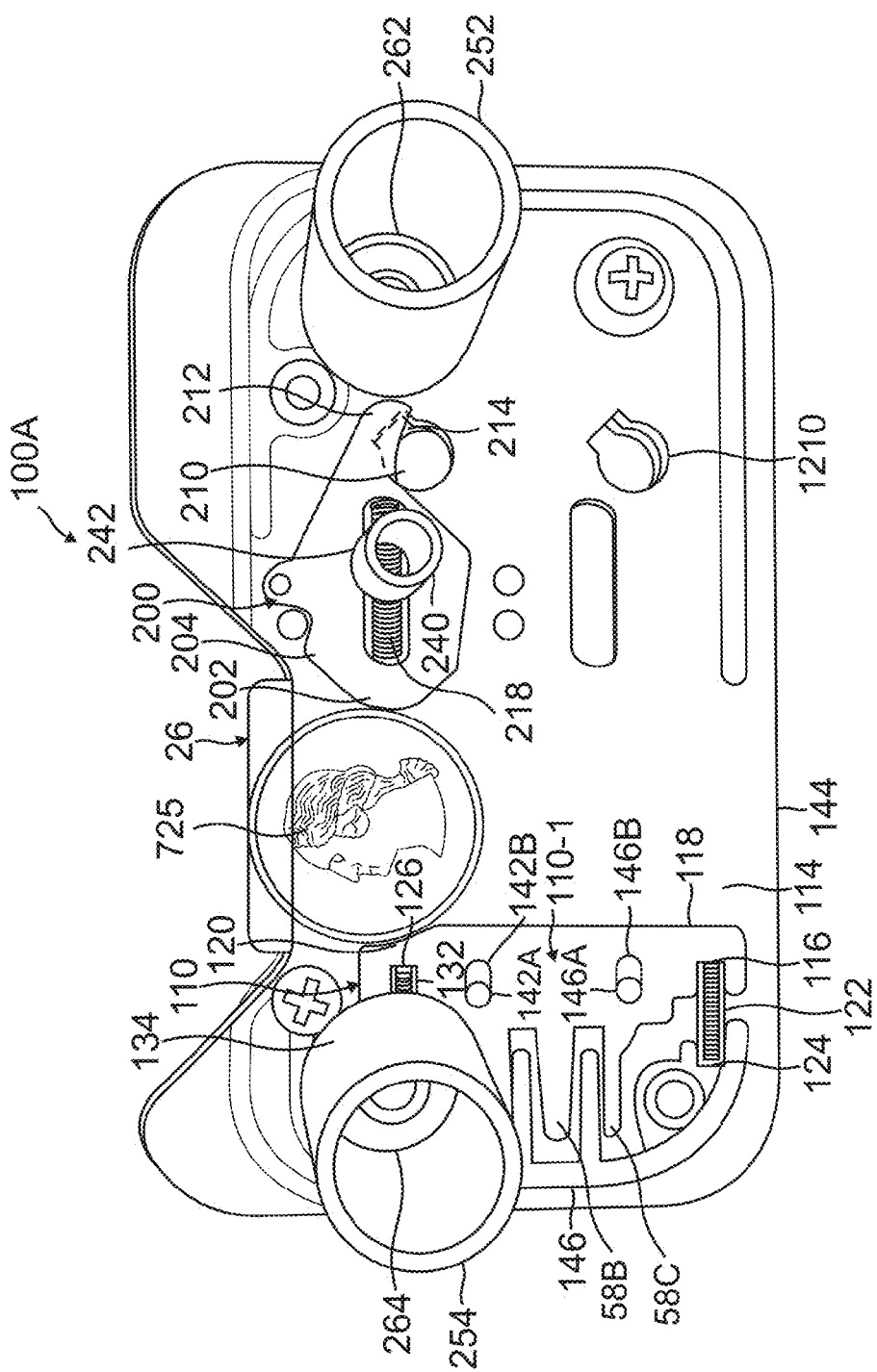
Figure 30:
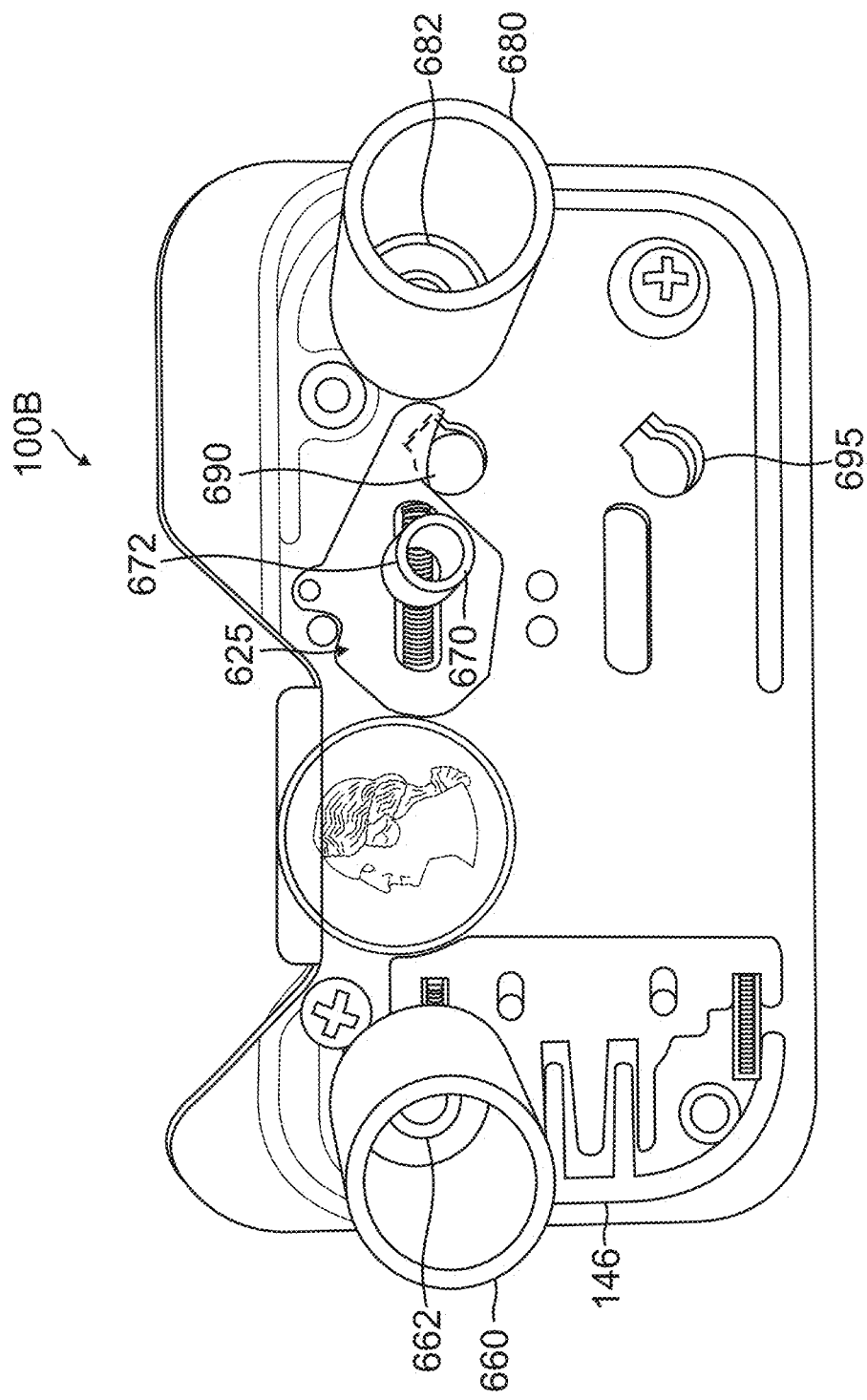
Figure 31:
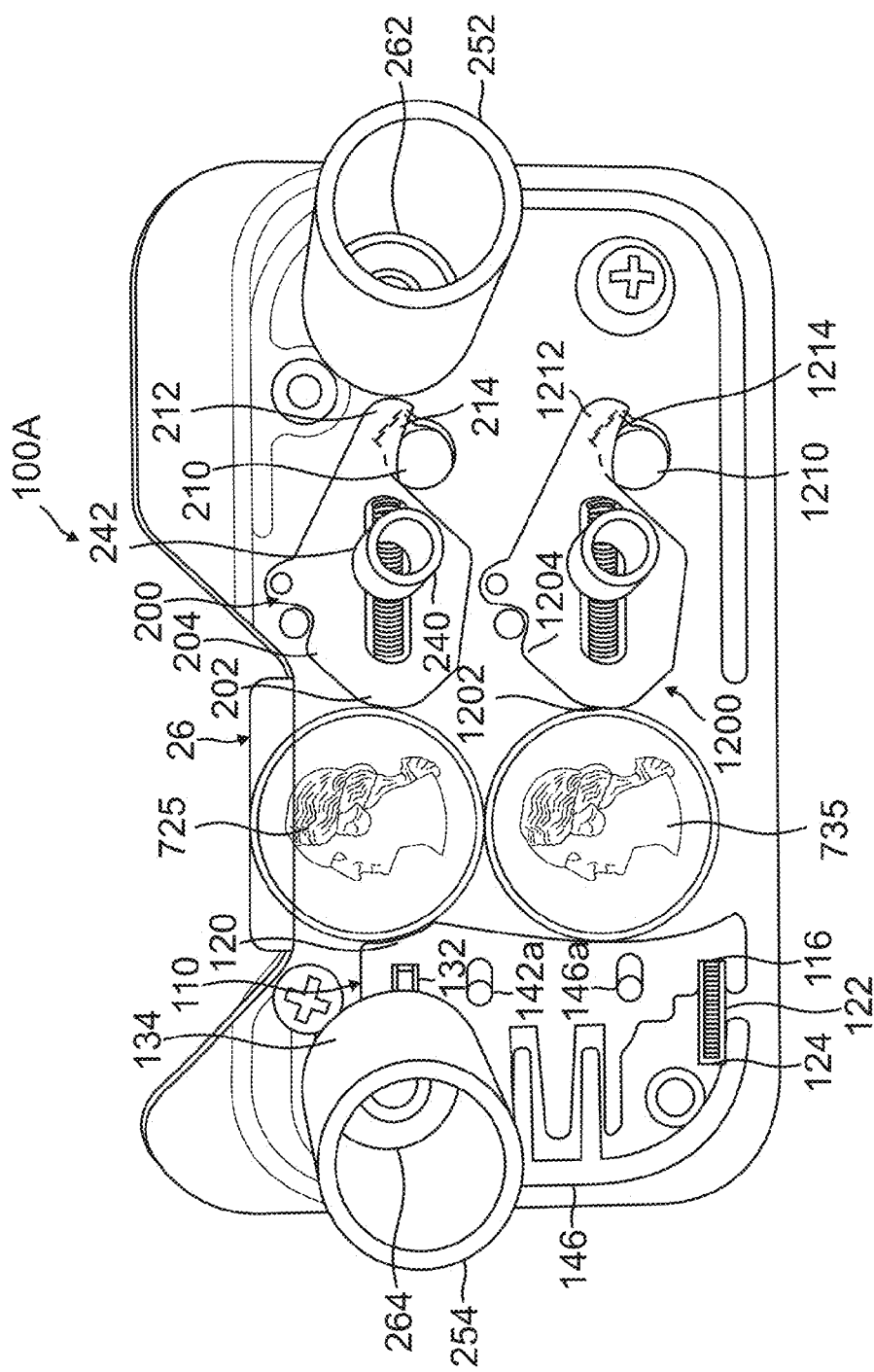
Figure 32:
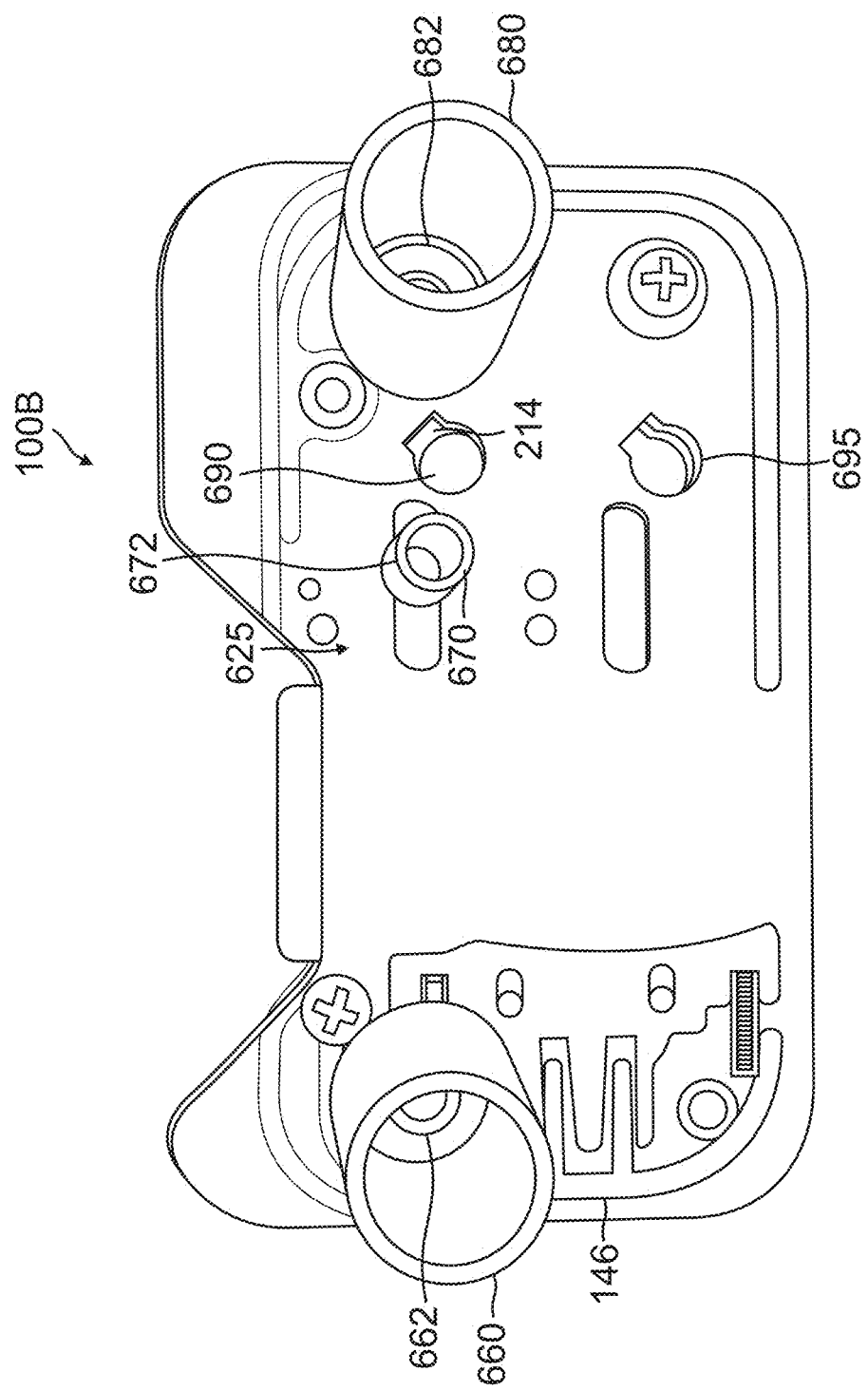
Figure 33:
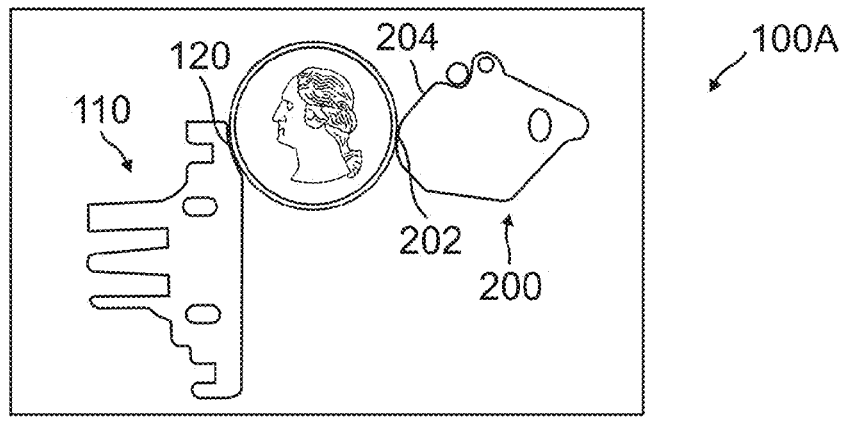
Figure 34:
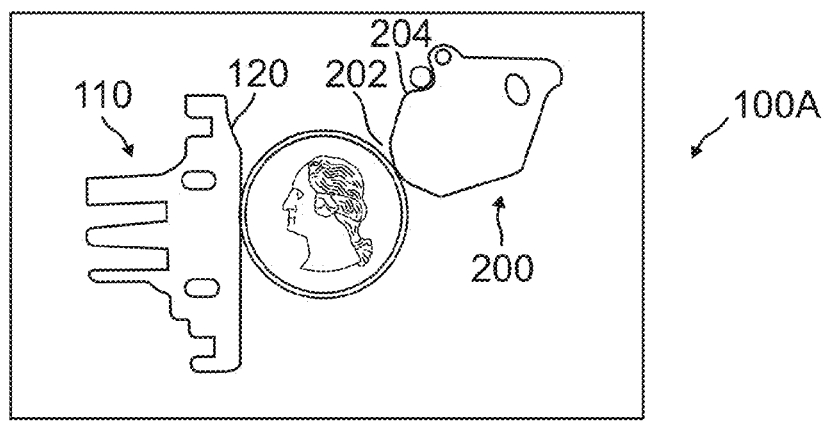
Figure 35:
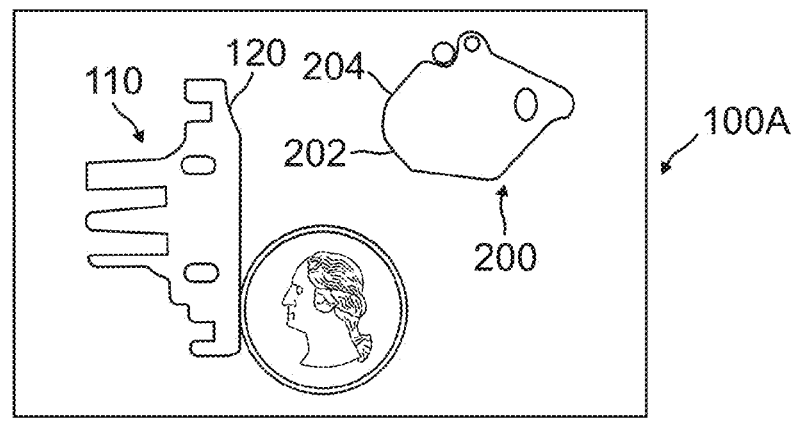

FIB. 13 is an exploded bottom perspective view of the pinion gear and sanitary napkin dispenser;

FIG. 14 is a bottom perspective view of the assembled pinion gear and sanitary napkin dispenser;

FIG. 15 is a top perspective open view of the sanitary napkin push rod;

FIG. 16 is a front perspective view of the front coin slot plate;

FIG. 17 an exploded front view of the coin slot assembly illustrating the rear coin slot plate, the middle coin slot plate and the front coin slot plate;

FIG. 18 is a rear perspective view of the front coin slot plate;

FIG. 19 is a rear perspective view of the middle coin slot plate;

FIG. 20 is a rear perspective view of the rear coin slot plate;

FIG. 21 is a front/top perspective view of the gear box cover;

FIG. 22 is a top/front perspective view of the module housing for both the sanitary napkin dispenser and the tampon dispenser;

FIG. 23 is a rear perspective view of the module housing including pinion gear, sanitary napkin dispenser, tampon dispenser and compression springs;

FIG. 24 is a front perspective view of the module housing including pinion gear, sanitary napkin dispenser, tampon dispenser and an exploded view of compression springs;

FIG. 25 is a front perspective view of the coin return plate for use with one coin;

FIG. 26 is a front perspective view of the coin return plate for use with two coins;

FIG. 27 is a perspective view of a cam;

FIG. 28 is a rear perspective view of the coin slot assembly with one cam for use with a tampon product or sanitary napkin (but numbers are for tampon product) at a cost of one quarter with no quarter in the coin slot, and also illustrating the coin return plate for two coins;

FIG. 29 is a rear perspective view of the coin slot assembly with one cam for use with a tampon product or sanitary napkin (but numbers are for tampon product) at a cost of one quarter with one quarter in the coin slot, and also illustrating the coin return plate for one coin;

FIG. 30 is a rear perspective view of the coin slot assembly with one cam for use with a tampon product or sanitary napkin (but numbers are for sanitary napkin) at a cost of one quarter with one quarter in the coin slot;

FIG. 31 is a rear perspective view of the coin slot assembly usable with two cams for use with a tampon product or sanitary napkin (but numbers are for tampon product) at a cost of two quarters with two quarters in the coin slot;

FIG. 32 is a rear perspective view of the coin slot assembly with no cams for use with a tampon product or sanitary napkin (but numbers are for sanitary napkin) at a cost of no quarters with no quarters in the coin slot;

FIG. 33 is a schematic of the coin slot assembly after a quarter is first inserted into the coin slot;

FIG. 34 is a schematic of the coin slot assembly when the cam has rotated slightly in the counterclockwise direction when the coin slot assembly is pushed inwards when the user purchases a product; and FIG. 35 is a schematic of the coin slot assembly after the quarter is released from the cam and the cam rotates clockwise by force of the cam compression spring to the cam's initial position.

DETAILED DESCRIPTION OF EMBODIMENTS OF THE PRESENT INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
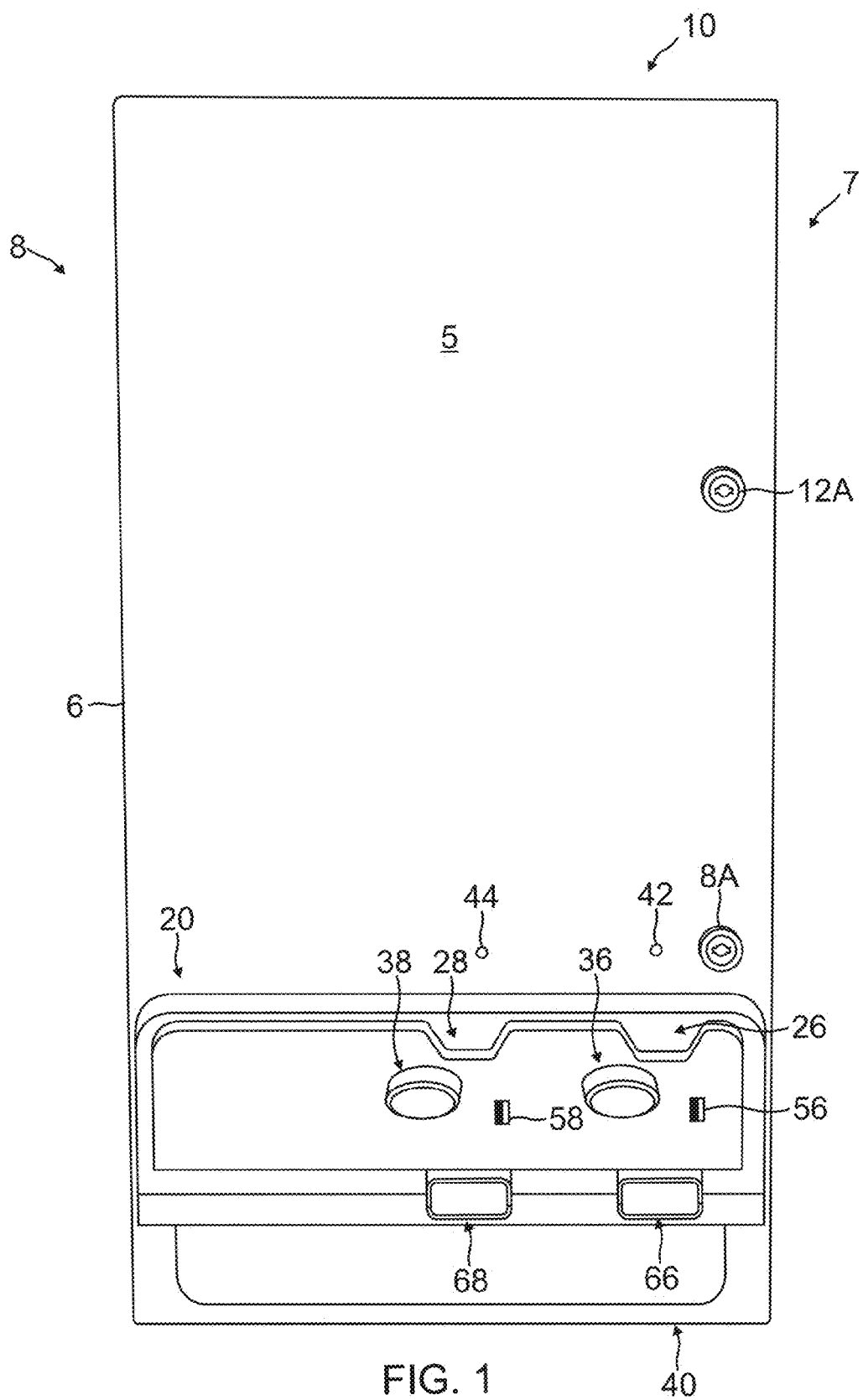
FIG. 1 is a front elevational view of the present invention with the door to the invention in the closed position.

Referring to FIG. 1, there is shown a front elevational view of the present invention feminine hygiene product dispenser 10 with its front door 7 closed. Located on cabinet 8 towards the bottom of front panel 5 of the present invention feminine hygiene product dispenser 10 is a front face plate 20. On the front face plate 20 is a first coin slot opening 26 located near the upper right corner of front face plate 20. First coin slot opening 26 is used in conjunction with first pushbutton 36 to dispense tampons from feminine hygiene product dispenser 10. Similarly, second coin slot opening 28 is used in conjunction with second pushbutton 38 to dispense sanitary napkins from feminine hygiene product dispenser 10. When each respective product is no longer available, first LED light 42 and second LED light 44 are activated by illuminating a visible light of at least one color, preferably, but not limited to, red. (The details of the sensor are discussed in more detail further below.)

Referring to FIGS. 1, 2, 3 and 4, the present invention is illustrated having a front door 7, inside back panel 9, bottom inside panel 17 (which makes up the flat surface of release tray 40), a first right side panel 13, a bottom panel 19, a first left panel 25, an inside right panel 27, and a top panel 23. Front door 7 contains a right door side panel 11A, a bottom door side panel 11B, a top door panel 11C, a left door panel 11D, and a rear door panel 15. Feminine hygiene product dispenser 10 is opened by rotating the front door 7 in a clockwise direction away from first side panel 13 by use of hinge 16. Feminine hygiene product dispenser 10 can be locked using first lock 8A in conjunction with lock retainer 8B to prevent front door 7 from opening. Also shown is second lock 12A where a second lock can be placed and used in conjunction with second lock retainer 12B.

The present invention feminine hygiene product dispenser 10 utilizes either a cam to purchase a product or a coin return plate to allow a user to have their quarter returned. When each respective pushbutton is used to purchase a product, a coin slot assembly (as further described in detail below) works in conjunction with a cam and releases the quarter after the coin slot assembly has moved a distance towards the center of the invention, thereby allowing the quarter to drop into a coin collection box. When a user decides to not purchase a product, then the coin return handle is utilized without the coin slot assembly moving inwards and the coin is released to the coin return tray. The functioning of the cam and the coin return plate are described in greater detail below.

Figure 3:
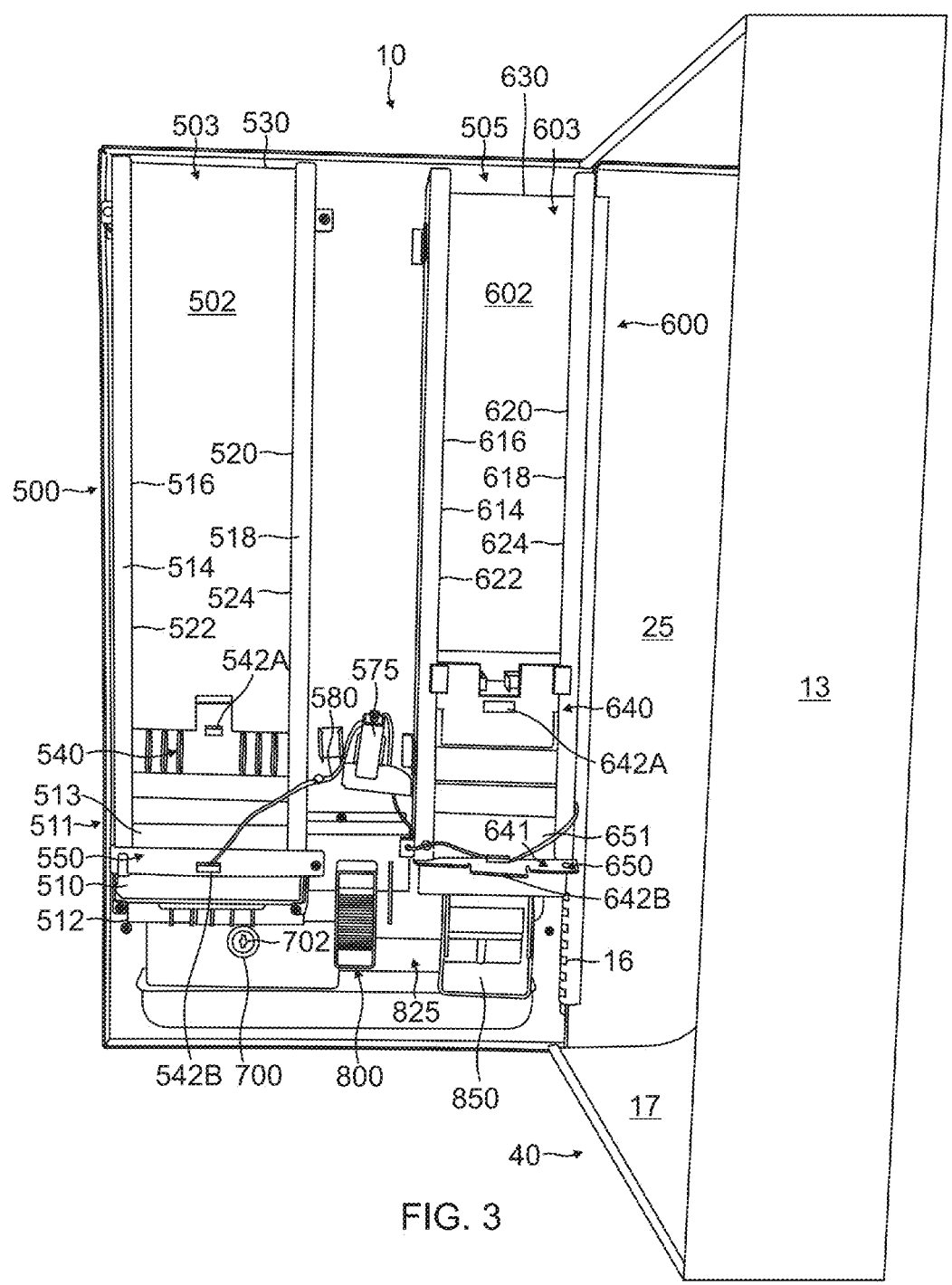
FIG. 3 is a front perspective view of the present invention with the door to the invention open and the invention rotated approximately 90 degrees from the view of FIG. 2.
Figure 4:
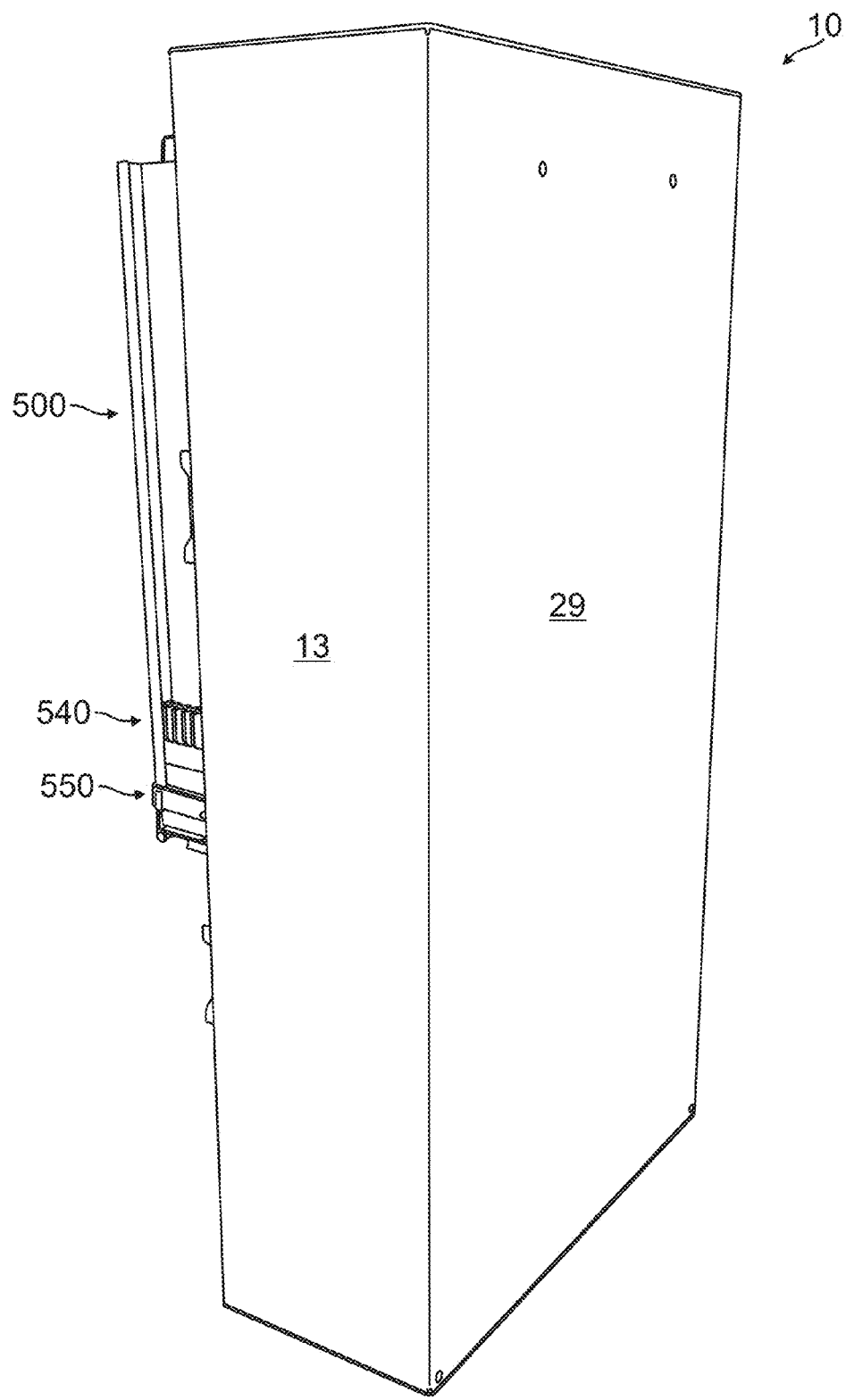
FIG. 4 is a rear perspective view of the present invention with the door to the invention open.

Further referring to FIG. 3, there are illustrated tampons being retained in tampon rack 500. The tampon rack has a tampon first front wall 514, a tampon second front wall 518, a tampon left side wall 516, a tampon right sidewall 520, a tampon back wall 502, a tampon left rear wall 522, and a tampon right rear wall 524. Tampons are placed inside tampon holder interior chamber 503 at tampon rack top 530 of tampon rack 500. A multitude of tampons can be placed inside tampon rack 500 as they are held in a stored position by tampon first front wall 514, tampon second front wall 518, tampon left side wall 516, tampon right sidewall 520, tampon back wall 502, tampon left rear wall 522, and tampon right rear wall 524. The first tampon sensor plate 550 retaining an out-of-product first sensor 542B is retained at the bottom 550 of tampon rack 500.

Figure 5:
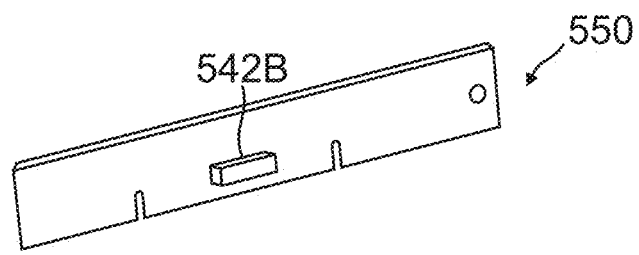
FIG. 5 is a perspective view of the tampon sensor retaining plate retaining an out-of-product sensor, which tampon sensor retaining plate is retained at a bottom of the tampon rack illustrated in FIG. 3.
Figure 12:
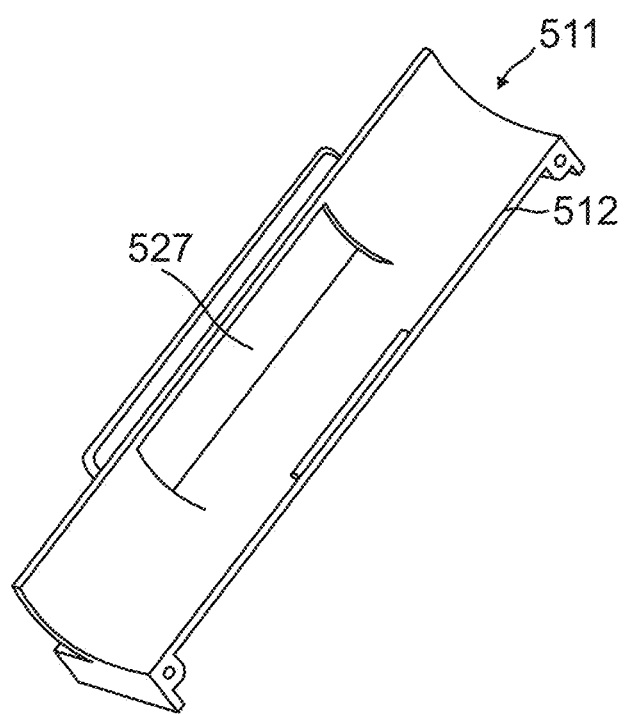
FIG. 12 top perspective view of the tampon tray with the tampon shelf.

Further illustrated in FIGS. 1 and 3 is a tampon weight 540 which retains an out-of-product first magnet 542A (see FIG. 6) which provides a downward force to keep a multiplicity of tampons in place and the lowest tampon member in a position to be pushed off of tampon shelf 512 of the tampon tray 11 (see FIG. 12). Tampon weight 540 provides an additional function by having a first magnet 542A that will illuminate first LED light 42 in a visible color including, but not limited to red, when first magnet 542A is facing and in proximity with first sensor 542B located on sensor plate 550 (see FIG. 5). Tampon weight 540 and sanitary napkin weight 640 provide an additional function by blocking the forward movement of first coin slot assembly 100A (illustrated in FIG. 28) when the present invention is out of tampons and second coin slot assembly 100B (illustrated in FIG. 30) when the present invention is out of sanitary napkins.

Figure 6:
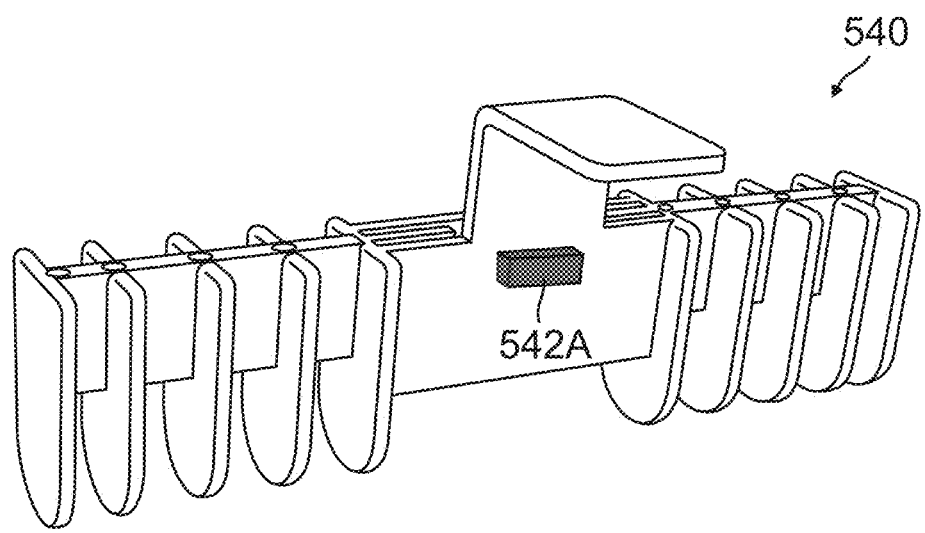
FIG. 6 is a perspective view of a tampon weight retaining an out-of-product first magnet.

As can be seen from tampon weight 540 in FIG. 6, there is a height associated with tampon weight 540 so that when there is no product remaining in tampon rack 500, from the components illustrated in FIGS. 2, 3, 5 and 6, first magnet 542A and first sensor 542B line up and face each other to complete a circuit using wires 580, battery 575 and first LED light 42. When this circuit is complete, first LED light 42 illuminates in a visible color, by way of example, the color red, which illumination is visible through LED light 42.

Figure 7:
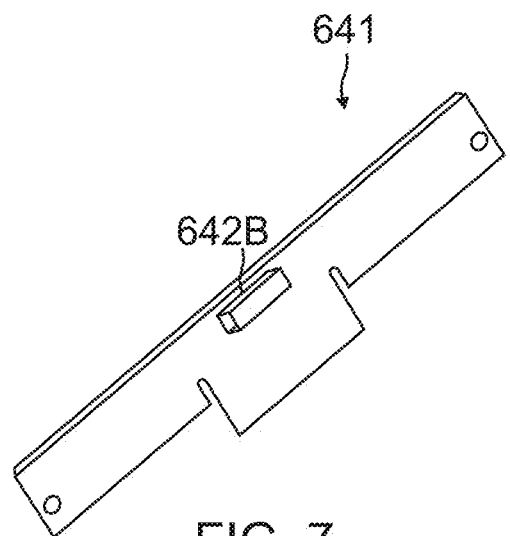
FIG. 7 is a perspective view of the feminine napkin sensor plate retaining an out-of-product second sensor, which feminine napkin sensor plate is retained at a bottom of the feminine napkin rack illustrated in FIG. 3.

Further referring to FIG. 3, there are illustrated sanitary napkins being retained in sanitary napkin rack 600. The sanitary napkin rack has a sanitary napkin first front wall 614, a sanitary napkin second front wall 618, a sanitary napkin left side wall 616, a sanitary napkin right sidewall 620, a sanitary napkin back wall 602, a sanitary napkin left rear wall 622, and a sanitary napkin right rear wall 624. Sanitary napkins are placed inside sanitary napkin holder interior chamber 603 at sanitary napkin rack top 630 of sanitary napkin rack 600. A multitude of sanitary napkins can be placed inside sanitary napkin rack 600 as they are held in a stored position by sanitary napkin first front wall 614, sanitary napkin second front wall 618, sanitary napkin left side wall 616, sanitary napkin right sidewall 620, sanitary napkin back wall 602, sanitary napkin left rear wall 622, and sanitary napkin right rear wall 624. The first sanitary napkin sensor plate 641 retaining an out-of-product second sensor 642B (see FIG. 7) is retained at the bottom of sanitary napkin rack 650.

Figure 8:
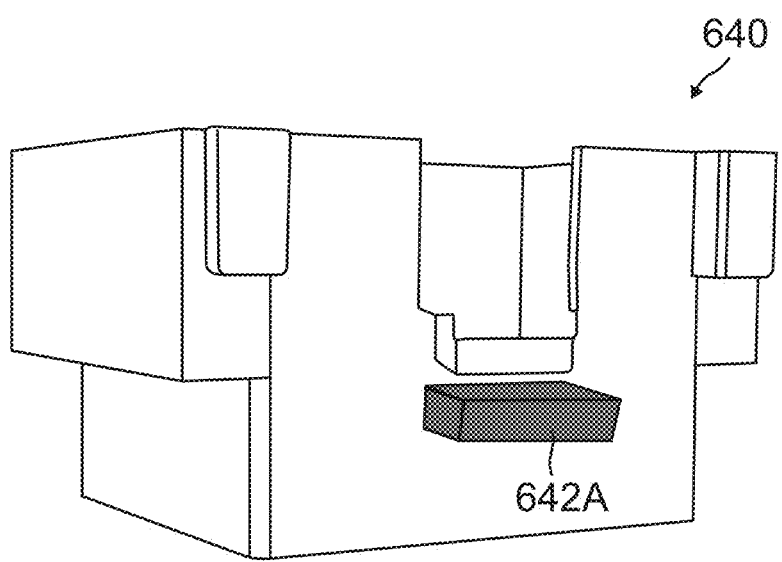
FIG. 8 is a perspective view of a feminine napkin weight retaining an out-of-product second magnet.

Further referring to FIGS. 1, 2, and 3, after there is no more sanitary napkin product, sanitary napkin weight 640 retaining second magnet 642A (see FIG. 8) comes to rest on the bottom of sanitary napkin rack 600 and on top of sanitary napkin dispenser 850 (as will be described). In this position, second magnet 642A and second sensor 642B on sanitary napkin sensor plate 641 (FIG. 7) line up and face each other to complete a circuit using wires 580, battery 575, and second LED light 44. When this circuit is complete, second LED light 44 illuminates in a visible color, by way of example, the color red. Sanitary napkin weight 640, when positioned at the bottom of sanitary napkin rack 600, prevents second coin slot assembly 100B (as will be described) from moving inward towards the center of the invention. This prevents the user of the invention from spending a quarter on a product when the invention is out of a product.

Figure 2:
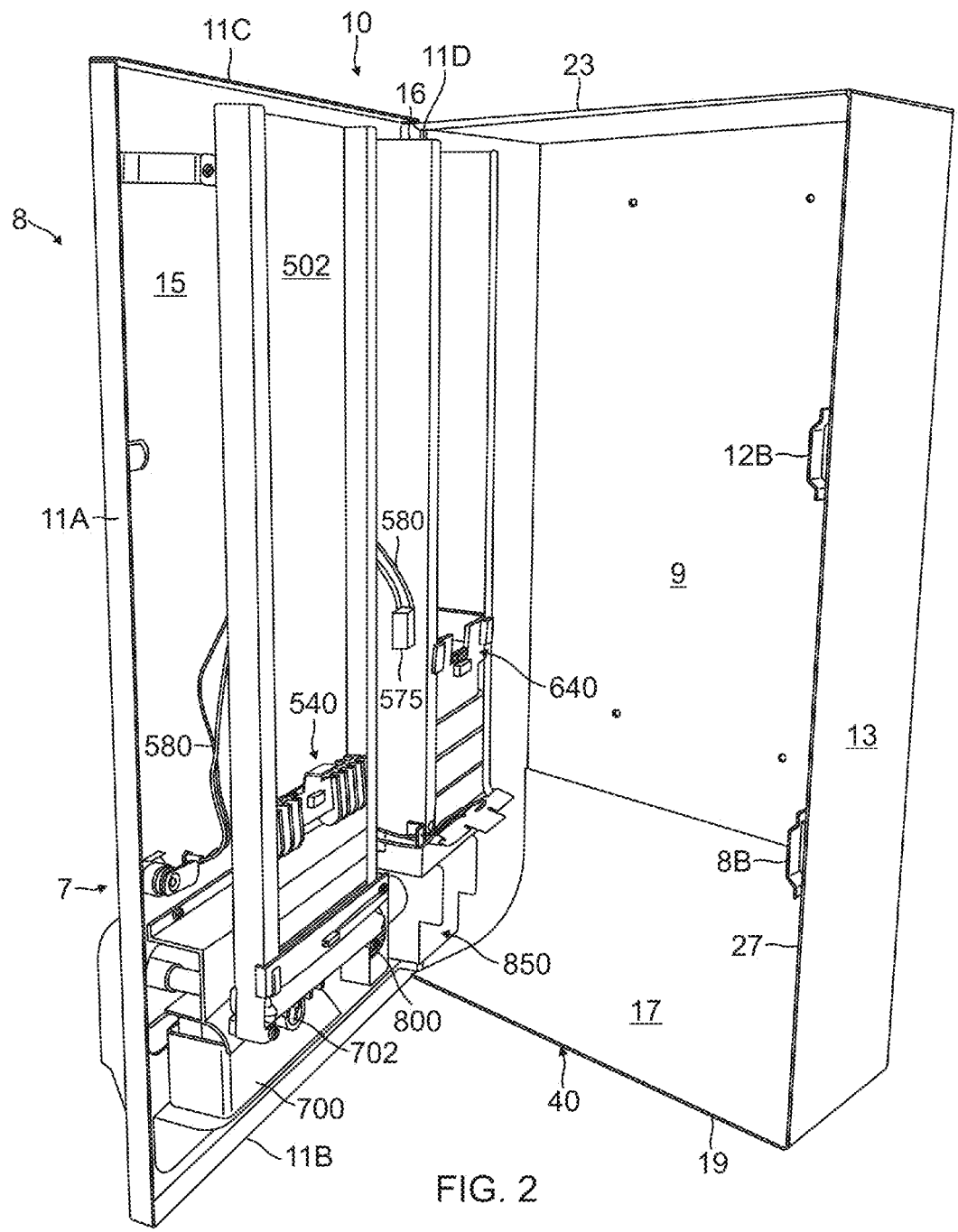
FIG. 2 is a front perspective view of the present invention with the door to the invention open.
Figure 9:
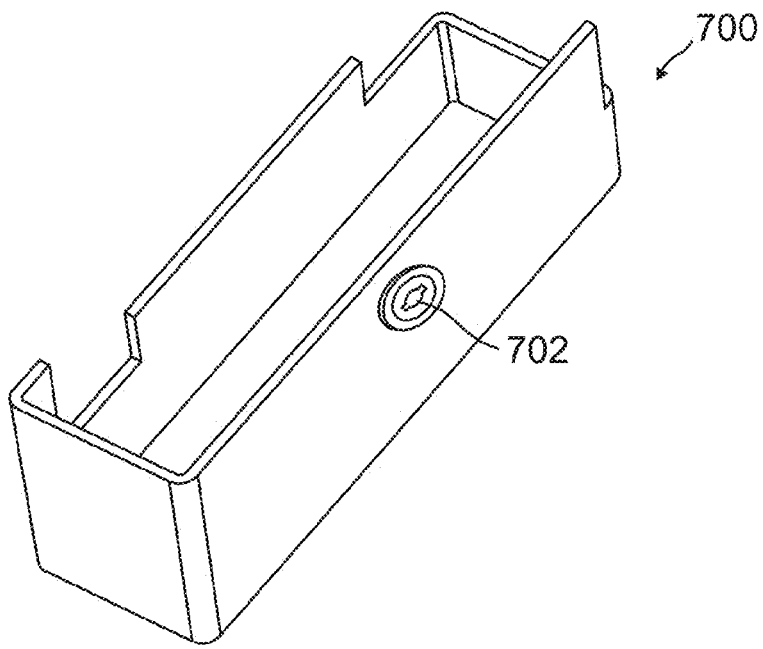
FIG. 9 is a top perspective view of the coin collection box.

Referring to FIG. 9, there is illustrated a top perspective view of the coin collection box 700 with coin collection box lock 702, also illustrated at the bottom of FIGS. 2 and 3.

Figure 10:
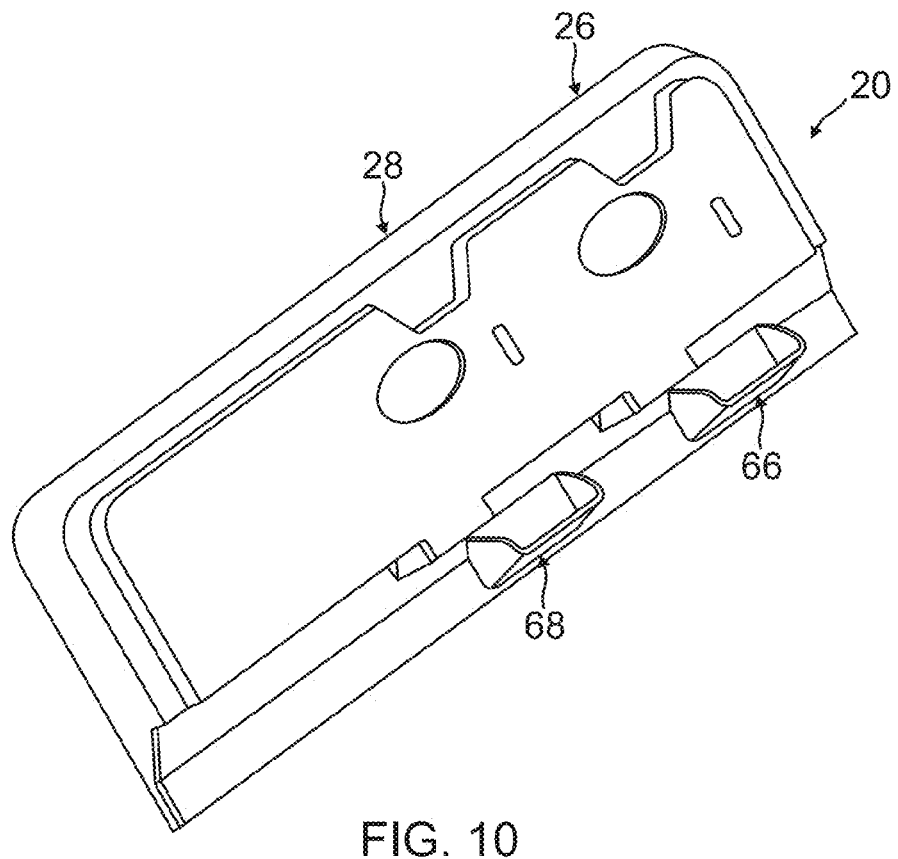
FIG. 10 is front perspective view of the front face plate.

Referring to FIG. 10, there is illustrated a front face plate having a first coin slot opening 26, a first coin return tray 66, a second coin slot opening 28 and a second coin return tray 68 (see FIG. 22).

Figure 11:
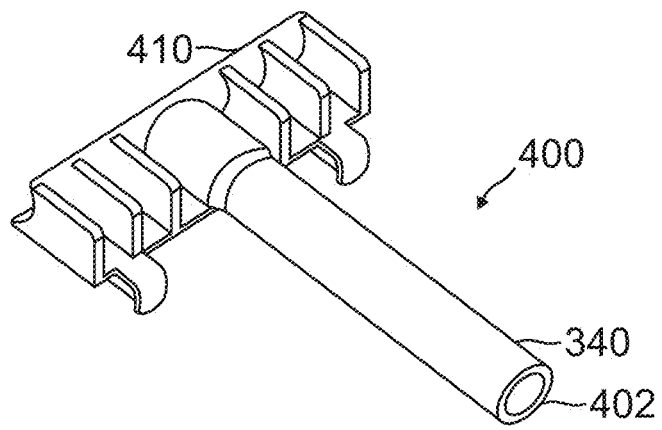
FIG. 11 is a top perspective view of the tampon pusher.

Referring to FIG. 11, there is illustrated a top perspective view of the tampon pusher 400 having a front curved face 410 with a cylindrical member 340 having a cylindrical opening 402.

Referring to FIG. 12, there is illustrated a top perspective view of the tampon tray 411 with tampon opening 527 and tampon shelf 512.

Figure 13:
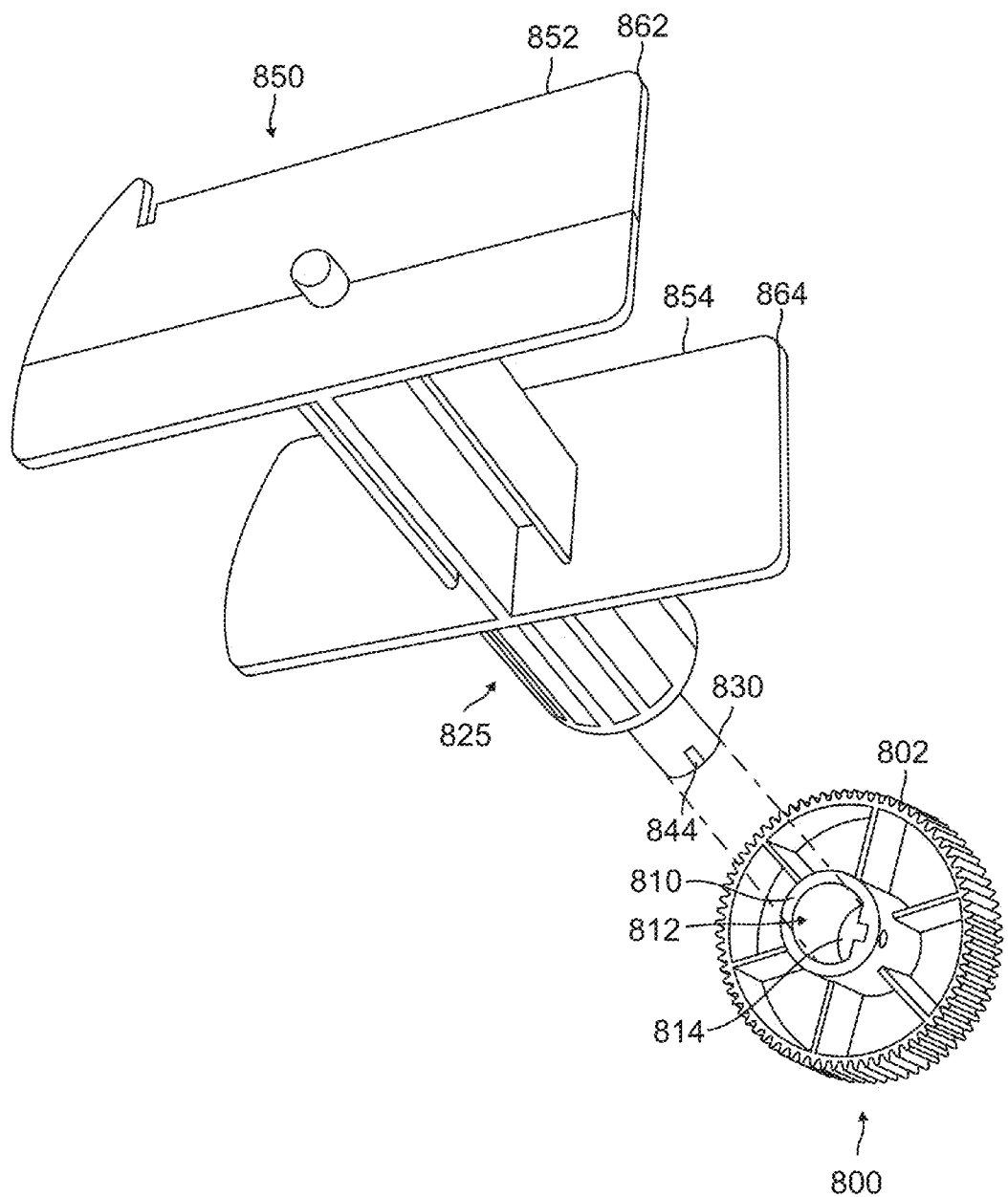

Referring to FIG. 13, there is illustrated a bottom perspective view of the sanitary napkin dispenser 850 and referring to FIG. 14 there is illustrated a bottom perspective view of the assembled sanitary napkin dispenser 850.

Sanitary napkin dispenser 850 attaches to module housing 300 by sanitary napkin pin 858 slidably inserted through and retained in module housing slot opening 397 (see FIG. 22 to be described). Referring to FIGS. 13 and 14, pinion gear 800 has a central hub 810 with a central opening 812 and a groove 814 in the wall of the central hub. Sanitary napkin dispenser 850 is integrally affixed to shaft 825. Shaft 825 has an end 830 with a tongue 844 adjacent end 830. Shaft 825 is connected to pinion gear 800 by means of tongue 844 of shaft end 830 press fitting snugly into groove 814 interior hub opening 812 with the remainder of the shaft end 830 press fit retained in central opening 812. Tongue section 844 of shaft end 830 prevents the pinion gear from slipping during rotation by fitting into groove section 814 of interior hub opening 812. As pinion gear 800 and shaft 825 rotate in unison, sanitary napkin dispenser 850 rotates as well.

Referring to FIG. 15, there is illustrated a top perspective open view of the sanitary napkin push rod 370 having cylinder 372 and teeth 374 which engage teeth 802 of pinion gear 800.

FIG. 16 is a front perspective view of the coin slot assembly. FIG. 17 is an exploded front view of the coin slot assembly illustrating the rear coin slot plate 140, the middle coin slot plate 180, and the front coin slot plate 160. FIG. 18 is a rear perspective view of the front coin slot plate. FIG. 19 is a rear perspective view of the middle coin slot plate 180. FIG. 20 is a rear perspective view of the rear coin slot plate 140.

Referring to FIGS. 1, 25 and 26, there is Illustrated in FIG. 25 a first coin return plate 110-1 or in FIG. 6 a second coin return plate 110-2 (which will be explained in other paragraphs) and a first coin return handle 56 which works in conjunction with a coin return tray 66 illustrated in FIG. 1. There is also a duplicate assembly with a second coin return handle 58 which works in conjunction with a second coin return tray 68, the remaining components being the same and to one side of the first coin return assembly. When a user decides not to purchase a product after inserting a quarter into first coin slot opening 26 or second coin slot opening 28 (see FIG. 10), the user has the ability to return the quarter(s) prior to making a purchase by utilizing first coin return handle 56 and/or second coin return handle 58.

The first coin dispensing assembly 100A is illustrated assembled for operation in the front perspective view of FIG. 16. To obtain a better understanding of the components, a front perspective view of the complete assembled first coin dispensing assembly 100A is illustrated in FIG. 16. A front perspective exploded view of main components of the first coin dispensing assembly is illustrated in FIG. 17. Rear perspective views of the same main components of the first coin dispensing assembly 100A, with certain parts numbered, are respectively illustrated in FIGS. 18, 19 and 20. A rear perspective view of first coin return plate 110-1 for use with a single coin such as a quarter is illustrated in FIG. 25. A rear perspective view of second coin return plate 110-2 for two coins such as two quarters is illustrated in FIG. 26. Referring to the figures identified in this paragraph, in FIG. 28, first coin slot assembly 100A is illustrated from a rear perspective view. Front coin slot plate 160, middle coin slot plate 180 and rear coin slot plate 140 and second coin return plate 110-2, come together to form a first coin slot assembly 100A as illustrated. First coin slot assembly 100A works in conjunction with first coin slot opening 26 to dispense tampons. There is a second coin slot assembly adjacent first coin slot assembly 100A located to the left behind front panel 20 that is not pictured in the Figures but functions identically to that of first coin slot assembly 100A. The second coin slot assembly works in conjunction with second coin slot opening 28 to dispense sanitary napkins.

Referring to FIG. 18, front coin slot plate 160 has a first aligned handle opening 156HA. Referring to FIG. 19, middle coin slot plate 180 has a first compression spring housing 122 and a second compression spring housing 132. Referring to FIG. 28, first compression spring 122CS is retained within first compression spring housing 122 between first endwall 116 and second endwall 124, with a portion of first compression spring 122CS extending transversely to wall 180W. Second compression spring 132CS is retained within second compression spring housing 132 between first endwall 126 and second endwall 134. Middle coin slot plate 180 also includes a second aligned handle opening 156HB, a top cam compression spring housing 219 surrounding an interior 1191 to house a cam compression spring 218, a first assembly top hole 210 surrounded by top hole housing 215 and bottom hole housing 1215 surrounding first assembly bottom hole 1210. Rear coin slot plate 140 includes the illustrated portions which extend inwardly toward middle coin slot plate 180 including an interior end wall 147 from which first fixed protrusion 147F1 and spaced apart second fixed protrusion 147F2 extend (147, 147F1 and 147F2 are shown in dashed lines in FIG. 20 because they extend from the opposite side of the wall 140W). Also illustrated in FIG. 20 are the fixed ends of spaced apart protrusions 146A and 142A (which also extend from the opposite side of the wall 140W), and which respectively extend through slotted openings 146B and 142B in first coin return plate, 110-1 and second coin return plate 110-2. Other components will be described in additional paragraphs.

Referring to FIGS. 20, 26 and 28, second coin return plate 110-2 is slidably affixed between middle coin slot plate 180 and rear coin slot plate 140, to be engaged by and slidably move between the slot plates. Second coin return plate 110-2 includes a second coin return plate lower notch 110-2LN which engages transversely extending portion of first compression spring 122CS and a second coin return plate upper notch 110-2UN which engages transverse extending portion of second compression spring 132CS. Concurrently, first protrusion 146A is inserted through first slot 146B and second protrusion 142A is inserted through second slot 142B. In addition, second coin return plate 110-2 has three spaced apart tabs 58A, 58B and 58C, with tab 58C located below lower fixed protrusion 147F2, tab 58B located between lower fixed protrusion 147F2 and upper fixed protrusion 147F1 and tab 58A located above upper fixed protrusion 147F1, with the tabs located at a distance from endwall 147. In addition, second coin retained plate 110-2 has an interior wall 1201 with an upper indent 120UI and a lower indent 118LI. First coin return plate 110-1 illustrated in FIG. 25 has a primarily straight interior wall 120S with only an upper indent 120 and a lower portion 118 being straight with no indent. In operation, handle 56 is moved toward endwall 147 with tabs 58A, 58B, and 58C slidably moving until they hit endwall 147 and are stopped and concurrently first protrusion 142A slidably moves through oval opening 142B and second protrusion 146B slidable moves through oval opening 146B until each respectively hit the portion of each oval opening closest to interior wall 1201. Concurrently, interior wall 1201 moves toward endwall 147 with indents 120UI and 118LI moving toward endwall 147. When the sliding motion is stopped, the handle 56 is released and compression return springs 122CS and 132CS which were compressed in their respective housings each exerts a return spring force to return second coin return plate 110-2 to its original position.

Referring to FIG. 27, there is illustrated a tampon top cam 200. This cam rotates in the counterclockwise direction when a user is purchasing a product. A quarter is held in position between tampon top cam first protrusion surface 202 and first coin return plate 100-1. When a user is purchasing a product, tampon top cam 200 rotates in the counterclockwise direction from an initial position when the quarter has been placed in first coin slot opening 26 and tampon top can first protrusion surface 202 is touching the quarter to a position of approximately 10 degrees in the counterclockwise direction so that tampon top cam first protrusion surface 202 is no longer in contact with the quarter. The functioning of the cam is discussed in further detail below.

Referring to FIG. 30, coin slot assembly 100B has a third cylindrical end wall 662 located on third exterior cylindrical member 660 and a fourth cylindrical endwall 682 located on fourth cylindrical member 680. Referring to FIG. 24, module housing 300 is illustrated having a combined sanitary napkin module and tampon module compression spring 362 that is retained between a first sanitary napkin cylindrical member 360 and third exterior end wall inside of third cylindrical member 660. Similarly, there is a first sanitary napkin module compression spring 382 that is retained between a second sanitary napkin cylindrical member 380 and fourth cylindrical end wall 682 inside of fourth cylindrical member 680.

FIG. 28 further shows the above described action. Second coin return plate 110-2 is slidably retained in an interior chamber between an interior of wall 140W and wall 180W. Second coin return plate 110-2 slides within the interior chamber until stopped as described above and returned to its original position as described above. The three components, rear coin slot plate 140, middle coin slot plate 180 and front coin slot plate 160 are all transparent so that FIG. 28 illustrates an open transparent view of the coin return assembly 100A. Further, middle coin slot plate 180 is affixed into front coin slot plate 160 and the rear coin slot plate 140 is affixed to front coin slot plate 160 so that a gap or interior chamber 114 is formed between an interior surface of wall 140W and wall 180W. The gap 114 is aligned with bottom slot opening 144 in front coin slot plate 160.

FIG. 28 further shows the above described action. Second coin return plate 110-2 is slidably retained in an interior chamber between an interior of wall 140W and wall 180W. Second coin return plate 110-2 slides within the interior chamber until stopped as described above and returned to its original position as described above. The three components, rear coin slot plate 140, middle coin slot plate 180 and front coin slot plate 160 are all transparent so that FIG. 28 illustrates an open transparent view of the coin return assembly 100A. Further, middle coin slot plate 180 is affixed into front coin slot plate 160 and the rear coin slot plate 140 is affixed to front coin slot plate 160 so that a gap or interior chamber 114 is formed between an interior surface of wall 140W and wall 180W. The gap 114 is aligned with bottom slot opening 144 in front coin slot plate 160.

First coin return plate 110-1 is illustrated in FIG. 29. Further illustrated in FIG. 29, when a quarter 725 is placed in first coin slot opening 26, the quarter is held in place by a notch 120 located on first coin return plate 110-1 and tampon top cam first protrusion surface 202 located on tampon top cam 200. These cams are spring loaded which creates pressure on the quarter 725 and prevents the quarter 725 from dropping and holds it in place. If the user decides to not purchase a product, the user can slide first coin return handle 56 on first coin return plate 110-1 to the right, compressing first compression spring 122CS and second compression spring 132CS. After first coin return plate 110-1 is displaced approximately half way to coin assembly endwall 147, the quarter 725 is no longer supported by and is no longer touching first notch 120. This causes the quarter 725 to slide down and through interior chamber 114 until it passes out of bottom slot opening 144 and into coin collection box 700. When the user releases first coin return handle 56, first compression spring 122CS and second compression spring 132CS force first coin return plate 110-1 back to its initial resting position.

Further illustrated in FIG. 29, in first coin slot assembly 100A there is a first assembly top hole 210 and tampon top cam closure end 212. Tampon top cam 200 is held in a non-rotating position in first coin slot assembly 100A by means of cam spring 218. This forces tampon top cam closure end 212 to partially cover first assembly top hole 210 and prohibits first coin slot assembly 100A from moving forward to dispense. When a quarter is inserted into first coin slot opening 26, the quarter exerts a downward force on tampon top cam 200 which causes tampon top cam 200 to rotate counterclockwise by a small distance (approximately 2 millimeters). This rotation causes tampon top cam closure end 212 to expose more of first assembly top hole 210. After first assembly top hole 210 has been exposed by the placement of a quarter inside of first coin slot opening 26 and a user presses in first pushbutton 36 on first coin slot assembly 100A, first coin slot assembly 100A moves inward towards the center of the invention.

Referring to FIGS. 24 and 28, as first coin slot assembly 100A moves inward, first cylindrical endwall 262 inside of first exterior transversely extending cylindrical member 252 fits inside of a first tampon cylindrical member 330 to compress a third compression spring 302, and second cylindrical endwall 264 inside of second exterior cylindrical member 254 fits inside of second tampon cylindrical member 314 to compress a fourth compression spring 304. Further, when first coin slot assembly 100A moves inward, first distal end 308 of upper tampon protruding member 312 enters first assembly top hole 210. When upper tampon protruding member 312 is further pushed into first assembly top hole 210, an upper tampon ribbed section 313 located on upper tampon protruding member 312 begins and displaces tampon top cam presser 214. As tampon top cam presser 214 is displaced by upper tampon protruding member 312 (see FIG. 22), more of first assembly top hole 210 is exposed. Tampon top cam presser 214 rests directly against tampon top cam closure end 212. The displacement of tampon top cam presser 214 causes the displacement of tampon top cam closure end 212 since these parts are pressed directly against each other. The displacement of tampon top cam closure cam end 212 by upper tampon protruding member 312 causes tampon top cam 200 to further rotate by an additional distance (approximately 4 millimeters). When tampon top cam 200 rotates from tampon top cam first protrusion surface 202 touching the quarter to tampon top cam second protrusion surface 204, this increases the distance between tampon top cam 200 and second coin return plate 110-2 (in FIG. 28) or first coin return plate 110-1 (in FIG. 29) which causes the quarter to no longer be held in position and to slide down and through interior chamber 114 until it passes out of bottom slot opening 144 and into coin collection box 700.

Schematic FIGS. 33, 34 and 35 summarize the operation of a cam by illustrating a quarter first entering the coin slot (FIG. 33), the cam rotating counter clockwise slightly when the coin slot assembly is pushed inward (FIG. 34), and the cam returning to its initial resting position prior to the insertion of a quarter and the quarter falling down and beginning to exit the coin slot assembly (FIG. 35).

Referring to FIG. 29, when the price of product is selected to be one coin, lower protruding tampon member 320 fits into first assembly bottom hole 1210 without the obstruction of tampon bottom cam presser 1214. When the price of product is selected to be two coins, then tampon bottom cam 1200 as shown in FIG. 31 is added below top cam 200. Tampon bottom cam 1200 functions identically to tampon top cam 200. When first coin slot assembly 100A moves inward, second distal end 318 of lower tampon protruding member 320 enters first assembly bottom hole 1210. When lower tampon protruding member 320 is further pushed into first assembly bottom hole 1210, a lower tampon ribbed section 321 (see FIG. 22) located on lower tampon protruding member 320 begins and displaces tampon bottom cam presser 1214. As tampon bottom cam presser 1214 is displaced by lower tampon protruding member 320, more of first assembly bottom hole 1210 is exposed. Tampon bottom cam presser 1214 rests directly against tampon bottom cam closure end 1212. The displacement of tampon bottom cam presser 1214 causes the displacement of tampon bottom cam closure end 1212 since these parts are pressed directly against each other. The displacement of tampon bottom cam closure cam end 1212 by lower tampon protruding member 320 causes tampon bottom cam 1200 to further rotate by an additional distance (approximately 4 millimeters). When tampon bottom cam 1200 rotates from tampon bottom cam first protrusion surface 1202 touching the quarter to tampon bottom cam second protrusion surface 1204, this increases the distance between tampon bottom cam 1200 and coin return plate 110-2 which causes the quarter to no longer be held in position and to slide down and through interior chamber 114 until it passes out of bottom slot opening 144 and into coin collection box 700. Both quarters, the first from cam 200 and the second from cam 1200, both involve the same process and both quarters fall into coin collection box 700.

Referring to FIGS. 11, 24, and 28, first assembly guide 240 fits into tampon cylinder opening 340 of tampon pusher 400. First guide pusher endwall 242 on first coin slot assembly 100A causes tampon pusher 400 to be displaced when first coin assembly 100A continues to move inward towards the center of the invention. Tampon pusher 400 has a front curved face 410 which is in direct contact with the lowest tampon member 510 in tampon rack 500 (see FIG. 3). When first coin slot assembly 100A is fully displaced towards inside back panel 9 of the invention, front curved face 410 on tampon pusher 400 (see FIG. 11) fits through tampon opening 527 (see FIG. 12) and pushes lowest tampon member 510 off tampon shelf 512 of tampon tray 511 (FIG. 12) and onto release tray 40 (see FIG. 2). FIG. 23 illustrates a first tampon pusher compression spring 515 and a second tampon pusher compression spring 517 that returns tampon pusher 400 to its initial condition when first pushbutton 36 (see FIG. 1) is released by user. After lowest tampon member 510 is pushed onto release tray 40, a second lowest tampon member 513 which resides directly above lowest tampon member 510 prior to being released drops onto tampon tray 511 and becomes the new lowest tampon member.

FIG. 3 further shows tampons being retained in tampon rack 500. The tampon rack has a tampon first front wall 514, a tampon second front wall 518, a tampon left side wall 516, a tampon right sidewall 520, a tampon back wall 502, a tampon left rear wall 522, and a tampon right rear wall 524. Tampons are placed inside tampon holder interior chamber 503 at tampon rack top 530 of tampon rack 500. A multitude of tampons can be placed inside tampon rack 500 as they are held in a stored position by tampon first front wall 514, tampon second front wall 518, tampon left side wall 516, tampon right sidewall 520, tampon back wall 502, tampon left rear wall 522, and tampon right rear wall 524.

Further illustrated in FIGS. 1 and 3 is a tampon weight 540 which has a first magnet 542A affixed to tampon weight 540 (see FIG. 6). Tampon weight 540 provides a downward force to keep a multiplicity of tampons in place and the lowest tampon member in a position to be pushed off of tampon shelf 512. Tampon weight 540 provides an additional function by having a first magnet 542A that will illuminate first LED light 42 in a visible color including, but not limited to red, when first magnet 542A is facing and in proximity with first sensor 542B located on sensor plate 550 (see FIG. 5). Tampon weight 540 and sanitary napkin weight 640 provide an additional function by blocking the forward movement of first coin slot assembly 100A when the present invention is out of tampons and second coin slot assembly 100B when the present invention is out of sanitary napkins.

As can be seen from tampon weight 540 in FIG. 6, there is a height associated with tampon weight 540 so that when there is no product remaining in tampon rack 500, from the components illustrated in FIGS. 2, 3, 5 and 6, first magnet 542A and first sensor 542B line up and face each other to complete a circuit using wires 580, battery 575, and first LED light 42. When this circuit is complete, first LED light 42 illuminates in a visible color, by way of example, the color red.

Referring to FIG. 30, coin slot assembly 100B has a third cylindrical endwall 662 located on third exterior cylindrical member 660 and a fourth cylindrical endwall 682 located on fourth exterior cylindrical member 680. Referring to FIG. 24 module housing 300 is illustrated having a fifth compression spring 362 that is retained between a first sanitary napkin cylindrical member 360 and third exterior end wall inside of third exterior cylindrical member 660. Similarly, there is a sixth compression spring 382 that is retained between a second sanitary napkin cylindrical member 380 and fourth cylindrical end wall 682 inside of fourth exterior cylindrical member 680. Identical to first coin slot assembly 100A, when second coin slot assembly 100B has a quarter in second coin slot opening 28, second pushbutton 38 located on second coin assembly 100B is pushed inward towards back panel 9. Identical to first coin slot assembly 100A, when second coin slot assembly 100B moves inward, fifth compression spring 362 and sixth compression spring 382 are compressed.

Further referring to FIG. 30, as second coin slot assembly 100B moves inward, upper napkin protruding member 390 enters second assembly top hole 690 on second coin slot assembly 100B. When upper napkin protruding member 390 has been inserted into second assembly top hole 690, an upper napkin ribbed section 392 located on upper napkin protruding member 390 causes napkin top cam 625 to rotate and release the quarter from second coin slot opening 28 (identical to first coin assembly 100A as explained previously in detail) and allows the quarter to fall into coin collection box 700 (see FIG. 9). The owner or operator of the vending machine can retrieve this quarter and any other previously inserted quarters used to purchase products by opening front door 7 and accessing coin collection box 700 by opening of coin collection box lock 702. An additional cam can be added to work in conjunction with second assembly bottom hole 695 if the operator or owner of this device wants to charge two quarters per product as opposed to one. This additional cam functions identically to tampon bottom cam 1200 as explained in detail above. Also, lower napkin protruding member 391 and lower napkin ribbed section 393 can be used in conjunction with a napkin lower cam and second assembly bottom hole 695.

Further referring to FIGS. 12, 26 and 30, there are illustrated components for the steps that as second guide pusher endwall 672 of second assembly guide pusher 670 displaces push rod cylinder 372 of push rod 370 (see FIG. 15), push rod teeth 374 interlock with pinion gear teeth 802 on pinion gear 800. When push rod 370 moves inward, this causes the rotation in a clockwise direction of pinion gear 800.

Referring to FIGS. 13 and 21, pinion gear 800 is protected by pinion gear cover plate 900 (see FIG. 21). Pinion gear cover plate 900 attaches to module housing 300 by first screw 901, second screw 902, third screw 903, fourth screw 904, and fifth screw 905. For purposes of clarity, cover plate 900 is not shown in FIG. 24. Opening 897 in cover plate 900 fits over 370 in FIG. 24. The respective screws fit through respective screw holes 901S, 902S, 903S, 904S, and 905S.

Referring to FIGS. 14 and 22, sanitary napkin dispenser 850 attaches to module housing 300 by napkin pin 858 slidably inserted through and retained in module housing slot opening 397. Referring to FIGS. 13 and 14, pinion gear 800 has a central hub 810 with a central opening 812 and a groove 814 in the wall of the central hub. Sanitary napkin dispenser 850 is integrally affixed to shaft 825. Shaft 825 has an end 830 with a tongue 844 adjacent end 830. Shaft 825 is connected to pinion gear 800 by means of tongue 844 of shaft end 830 press fitting snugly into groove 814 interior hub opening 812 with the remainder of the shaft end 830 press fit retained in central opening 812. Tongue section 844 of shaft end 830 prevents the pinion gear from slipping during rotation by fitting into groove section 814 of interior hub opening 812. As pinion gear 800 and shaft 825 rotate in unison, sanitary napkin dispenser 850 rotates as well. At resting position (prior to second coin assembly 100B moving inwards) lowest sanitary napkin member 650 (shown in FIG. 3) is flat or at zero degrees resting upon and across a first top dispenser surface 852 and a second top dispenser surface 854 (see FIG. 13). When second pushbutton member 38 is pressed in and second coin assembly 100B moves inwards, pinion gear 800 and shaft 825 rotate the sanitary napkin dispenser in a clockwise direction. When second coin assembly 100B is pressed inwards to its maximum possible displacement, sanitary napkin dispenser 850 has rotated approximately 60 degrees. By the force of gravity at this inward position, lowest sanitary napkin member 650 slides on first top dispenser surface 852 and second top dispenser surface 854 towards back panel 9 and in a downwards direction. After the entire sanitary napkin bottom surface 652 of lowest sanitary napkin member 650 has slid past first top edge 862 and a second top edge 864, the lowest sanitary napkin member 650 falls onto release tray 40. When second pushbutton 38 is released by the user, the force of tension spring 822 (see FIG. 24) returns sanitary napkin dispenser 850 to its initial flat position. Then, sanitary napkin weight 640 combined with the weight of the other napkins forces the second lowest sanitary napkin member 651 onto sanitary napkin dispenser 850 to become lowest sanitary napkin member 650. This process is repeated until there is no more sanitary napkin product.

Further referring to FIGS. 1, 2, and 3, after there is no more sanitary napkin product, sanitary napkin weight 640 (see FIG. 8) comes to rest on the bottom of sanitary napkin rack 600 and on top of sanitary napkin dispenser 850. In this position, second magnet 642A and second sensor 642B on second sensor plate 641 (FIG. 7) line up and face each other to complete a circuit using wires 580, battery 575, and second LED light 44. When this circuit is complete, second LED light 44 illuminates in a visible color, by way of example, the color red. Sanitary napkin weight 640, when positioned at the bottom of sanitary napkin rack 600, prevents second coin slot assembly 100B from moving inward towards the center of the invention. This prevents the user of the invention from spending a quarter on a product when the invention is out of a product.

Of course the present invention is not intended to be restricted to any particular form or arrangement, or any specific embodiment, or any specific use, disclosed herein, since the same may be modified in various particulars or relations without departing from the spirit or scope of the claimed invention herein above shown and described of which the apparatus or method shown is intended only for illustration and disclosure of an operative embodiment and not to show all of the various forms or modifications in which this invention might be embodied or operated.

What is claimed is:

1. An apparatus to retain and dispense feminine hygiene products, the apparatus comprising:
   a. a cabinet with an exterior having a front door, a back panel, a left side panel, a right side panel, a top panel, and a bottom panel and said front door of said cabinet having a front panel, a bottom door panel, a top door panel, right door side panel a left door side panel, and a rear door panel with a sanitary napkin rack and a tampon rack affixed to said rear door panel;
   b. said tampon rack formed from a tampon first front wall, a tampon second front wall, a tampon left side wall, a tampon right sidewall, a tampon back wall, a tampon left rear wall, and a tampon right rear wall and said tampon rack retaining a multiplicity of vertically aligned tampons, a tampon weight including a tampon magnet with said tampon weight exerting a downward force on the multiplicity of tampons when removably placed onto an uppermost tampon in said tampon rack, a tampon sensor plate affixed to and at a location adjacent to the bottom of said tampon rack, said tampon sensor plate having a tampon sensor that mates with said tampon magnet, whereby when said tampon rack is out of tampons and said tampon magnet and said tampon sensor are aligned, an electrical circuit is closed and a tampon light is illuminated whereby illumination of tampon light is visible from said front panel;

c. a sanitary napkin rack formed from a sanitary napkin first front wall, a sanitary napkin second front wall, a sanitary napkin left side wall, a sanitary napkin right sidewall, a sanitary napkin back wall, a sanitary napkin left rear wall, and a sanitary napkin right rear wall and said sanitary napkin rack retaining a multiplicity of vertically aligned sanitary napkins, a sanitary napkin weight including a sanitary napkin magnet with said napkin weight exerting a downward force on the multiplicity of sanitary napkins when removably placed onto an uppermost sanitary napkin in said sanitary napkin rack, a sanitary napkin sensor plate affixed to and at a location adjacent to the bottom of said sanitary napkin rack, said sanitary napkin sensor plate having a sanitary napkin sensor that mates with said sanitary napkin magnet, whereby when said sanitary napkin rack is out of sanitary napkins and said sanitary napkin magnet and said sanitary napkin sensor are aligned, an electrical circuit is closed and a napkin light is illuminated whereby illumination of napkin light is visible from said front panel;

d. said front panel having a front face plate with a first coin slot opening working in conjunction with a first push button, a first coin slot assembly, a first coin return handle, and a first coin return tray, and a second coin slot opening working in conjunction with a second push button, a second coin slot assembly, a second coin return handle, and a second coin return tray;

e. said first coin slot assembly contains a front coin slot plate having a first aligned handle opening, a middle coin slot plate having a wall with a first coin slot compression spring housing retaining a first coin slot compression spring and a second coin slot compression spring housing retaining a second coin slot compression spring, said middle coin slot plate having a second aligned handle opening, a top cam compression spring housing retaining a top cam compression spring, a first assembly top hole surrounded by a top hole housing and a bottom cam compression spring housing retaining a bottom cam compression spring, a first assembly bottom hole surrounded by a bottom hole housing, and a rear coin slot plate including a lower fixed protrusion and an upper fixed protrusion;

f. said coin return plate includes three spaced apart tabs and a coin return plate upper notch which engages said transverse extending portion of second compression spring, whereby a coin can be returned to a user by sliding said coin return plate;

g. a tampon pusher having a front curved face directly adjacent a lowest tampon member in said tampon rack, and when first coin slot assembly is fully displaced towards said inside back panel, said front curved face fits through a tampon opening and pushes said lowest tampon member off a tampon tray;

h. a sanitary napkin push rod including push rod teeth that interlock with pinion gear teeth on a pinion gear with said pinion gear having a central hub affixed to a shaft that is affixed to a sanitary napkin dispenser, and when said sanitary napkin push rod moves inward towards said back panel, said pinion gear, said shaft, and said sanitary napkin dispenser rotate in unison in the clockwise direction;

i. a distance between an upper indent on said coin return plate and top cam first protrusion surface on a top cam is less than the largest diameter of a United States quarter; and j. a distance between said upper indent on said coin return plate and a top cam second protrusion surface on said top cam is greater than the largest diameter of a United States quarter.

\* \* \* \* \*